(12) United States Patent
Oishi et al.

(10) Patent No.: US 9,511,565 B2
(45) Date of Patent: Dec. 6, 2016

(54) POLYIMIDE PRECURSOR, POLYIMIDE, POLYIMIDE FILM, AND METHOD FOR MANUFACTURING TRIAZINE COMPOUND USED FOR MANUFACTURING SAME

(75) Inventors: Yoshiyuki Oishi, Morioka (JP); Nobuharu Hisano, Ube (JP); Shin-ichiro Kohama, Ube (JP); Taizou Murakami, Ube (JP); Hiroaki Yamaguchi, Ube (JP)

(73) Assignees: UBE INDUSTRIES, LTD., Ube-Shi (JP); NATIONAL UNIVERSITY CORPORATION IWATE UNIVERSITY, Morioka-Shi (JP)

( * ) Notice: Subject to any disclaimer, the term of this patent is extended or adjusted under 35 U.S.C. 154(b) by 425 days.

(21) Appl. No.: 14/237,976

(22) PCT Filed: Aug. 10, 2012

(86) PCT No.: PCT/JP2012/070517
§ 371 (c)(1),
(2), (4) Date: May 19, 2014

(87) PCT Pub. No.: WO2013/024820
PCT Pub. Date: Feb. 21, 2013

(65) Prior Publication Data
US 2014/0255710 A1    Sep. 11, 2014

(30) Foreign Application Priority Data
Aug. 12, 2011    (JP) .................................. 2011-177133

(51) Int. Cl.
*B32B 15/08*    (2006.01)
*B32B 7/12*    (2006.01)
(Continued)

(52) U.S. Cl.
CPC ................. *B32B 7/12* (2013.01); *B32B 15/08* (2013.01); *B32B 15/088* (2013.01); *B32B 15/20* (2013.01);
(Continued)

(58) Field of Classification Search
CPC ... C08G 73/1085; C08G 69/26; C07D 251/54; C07D 251/70; B32B 27/281; B32B 7/12; B32B 15/12; B32B 2427/00; Y10T 428/31678
See application file for complete search history.

(56) References Cited

U.S. PATENT DOCUMENTS 3,666,723 A    5/1972    Kray et al.
3,729,448 A    4/1973    Seltzer et al.
(Continued)

FOREIGN PATENT DOCUMENTS

CN    101160207 A    4/2008
JP    B-S48-8272    3/1973
(Continued)

OTHER PUBLICATIONS

STIC Search Report dated Jun. 3, 2016.*
(Continued)

*Primary Examiner* — Eisa Elhilo
(74) *Attorney, Agent, or Firm* — Knobbe Martens Olson & Bear LLP

(57) ABSTRACT

A polyimide precursor for obtaining a polyimide film having excellent adhesiveness to metals and improved transmittance in the UV-visible range, a polyimide in which the polyimide precursor is used, a polyimide film in which the polyimide is used, and a method for manufacturing a triazine compound used for manufacturing the polyimide precursor, polyimide film and polyimide.

14 Claims, 2 Drawing Sheets

(51) Int. Cl.
  C07D 251/54 (2006.01)
  C07D 251/70 (2006.01)
  C08G 73/10 (2006.01)
  B32B 27/28 (2006.01)
  B32B 15/088 (2006.01)
  C08G 69/26 (2006.01)
  B32B 15/20 (2006.01)
  B32B 27/18 (2006.01)
  C08G 73/06 (2006.01)

(52) U.S. Cl.
  CPC ............. *B32B 27/18* (2013.01); *B32B 27/281* (2013.01); *C07D 251/54* (2013.01); *C07D 251/70* (2013.01); *C08G 69/26* (2013.01); *C08G 73/0644* (2013.01); *C08G 73/1039* (2013.01); *C08G 73/1053* (2013.01); *C08G 73/1064* (2013.01); *C08G 73/1067* (2013.01); *C08G 73/1071* (2013.01); *C08G 73/1085* (2013.01); *B32B 2264/10* (2013.01); *B32B 2307/20* (2013.01); *B32B 2307/306* (2013.01); *B32B 2307/412* (2013.01); *B32B 2307/50* (2013.01); *B32B 2307/714* (2013.01); *B32B 2307/748* (2013.01); *B32B 2457/00* (2013.01); *B32B 2457/08* (2013.01); *Y10T 428/31678* (2015.04); *Y10T 428/31681* (2015.04)

(56) References Cited

U.S. PATENT DOCUMENTS 3,755,322 A * 8/1973 Winter .................. C07D 251/52
  544/196
3,803,075 A * 4/1974 Kray .................. C08G 73/1085
  428/366
2002/0098378 A1 7/2002 Kim et al.
2002/0132133 A1 9/2002 Kim et al.
2004/0266979 A1 12/2004 Oguro et al.
2009/0035541 A1 2/2009 Yokozawa et al.
2014/0066571 A1 3/2014 Takasawa et al.

FOREIGN PATENT DOCUMENTS

| JP | 52-3388 | * | 1/1977 | ........... C07D 251/18 |
| JP | B-S52-3388 | | 1/1977 | |
| JP | A-2001-023778 | | 1/2001 | |
| JP | A-2002-161136 | | 6/2002 | |
| JP | A-2002-348374 | | 12/2002 | |
| JP | A-2005-015629 | | 1/2005 | |
| JP | A-2009-087763 | | 4/2009 | |
| JP | A-2009-263570 | | 11/2009 | |
| JP | A-2010-031102 | | 2/2010 | |
| JP | A-2011-037818 | | 2/2011 | |
| JP | A-2011-102259 | | 5/2011 | |
| WO | WO 2012/124664 | | 9/2012 | |

OTHER PUBLICATIONS

International Preliminary Report on Patentability issued in PCT/JP2012/070517 mailed Feb. 27, 2014.

International Search Report issued in PCT/JP2012/070517 on Nov. 6, 2012.

Office Action in Taiwanese Patent Application No. 101129030, dated Feb. 17, 2016.

* cited by examiner

POLYIMIDE PRECURSOR, POLYIMIDE, POLYIMIDE FILM, AND METHOD FOR MANUFACTURING TRIAZINE COMPOUND USED FOR MANUFACTURING SAME

This application is the U.S. National Phase under 35 U.S.C. §371 of International Application No. PCT/JP2012/070517, filed Aug. 10, 2012, designating the U.S., and published in Japanese as WO 2013/024820 on Feb. 21, 2013, which claims priority to Japanese Patent Application No. 2011-177133 filed Aug. 12, 2011, the entire contents of which are incorporated herein by reference.

TECHNICAL FIELD

The present invention relates to a polyimide precursor and a polyimide, particularly a polyimide film excellent in adhesiveness with a metal and having an improved transparency in UV-visible range and a method for manufacturing triazine compound used for manufacturing these.

BACKGROUND ART

A polyimide film has been extensively used in the fields of electric/electronic devices, semiconductors and so on, because of its excellent heat resistance, chemical resistance, mechanical strength, electric properties, dimensional stability and so on. For example, for a flexible printed circuit board (FPC), there has been used a copper-clad laminated substrate where a copper foil is laminated on one or both sides of a polyimide film.

In general, a polyimide film may not, however, provide a laminate having adequately high peeling strength when a metal layer is formed on a polyimide film by dry plating such as metal deposition and sputtering, or when a metal layer is formed on a polyimide film by wet plating such as electroless plating.

In recent years, there has been investigated plastic substrates that are light and flexible as a replacement of a glass substrate in a field of optical materials, for example, a display field, and therefore optical materials having higher performance have been demanded. For example, methods of expressing transparency by using semi-alicyclic or wholly alicyclic polyimide resins are proposed (Patent Documents 1 to 3). For example, semi-alicyclic polyimides prepared using trans-1,4-diaminocyclohexanes as a diamine component and 3,3',4,4'-biphenyltetracarboxylic dianhydrides as a tetracarboxylic acid component are known (Patent Document 3).

Patent Document 4 has described a polyimide from a triazine-based diamine, showing an example in which a polyimide solution is applied on a metal foil. In addition, as examples of the use of a triazine-based diamine, Patent Document 5 has disclosed an end-modified imide oligomer using a triazine-based diamine and Patent Document 6 has disclosed a polymer electrolyte using a triazine-based diamine. Patent Document 7 discloses a polyimide which uses a triazine-based diamine having two amino groups (—NH₂) in para-positions in benzene rings relative to two NH groups bonded to the triazine rings (hereinafter, it may be referred as "p-ATDA").

PRIOR ART REFERENCES

Patent Documents

Patent Document 1: Japanese Patent Laid-Open No. 2002-348374

Patent Document 2: Japanese Patent Laid-Open No. 2005-15629

Patent Document 3: Japanese Patent Laid-Open No. 2002-161136

Patent Document 4: U.S. Pat. No. 3,803,075

Patent Document 5: Japanese Patent Laid-Open No. 2009-263570

Patent Document 6: Japanese Patent Laid-Open No. 2009-87763

Patent Document 7: Japanese Patent Laid-Open No. 2010-31102

Patent Document 8: Japanese Examined Patent Publication No. S 48-8272

SUMMARY OF THE INVENTION

Problem to be Solved by the Invention

As mentioned above, in spite of the proposal for obtaining a highly transparent polyimide, the physical properties of the polyimide film are inferior to those of wholly aromatic polyimide. Therefore, a method of improving the transparency of polyimide by using aromatic diamines is advantageous in terms of its physical properties.

Namely, an object of the present invention is to provide a polyimide precursor for obtaining a polyimide film having excellent adhesiveness to metals and improved transmittance in the UV-visible range, a polyimide in which the polyimide precursor is used, a polyimide film in which the polyimide is used, and a method for manufacturing a triazine compound used for manufacturing the polyimide precursor, the polyimide, and the polyimide film.

Means for Solving the Problem

The present invention relates to the followings items.

1. A polyimide precursor comprising a structural unit represented by general formula (I):

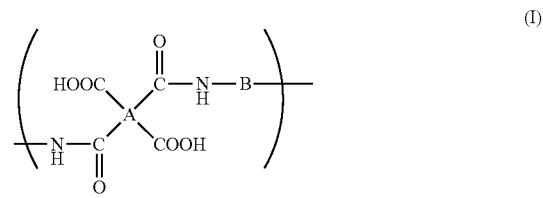

(in which A is a tetravalent aromatic group or aliphatic group and B is a divalent aromatic group), wherein B in general formula (I) comprises a triazine moiety represented by following formula (B1):

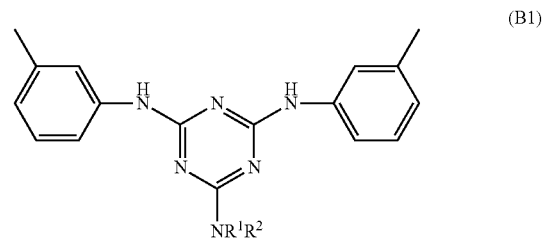

(in which R¹ denotes hydrogen or alkyl or aryl having 1 to 12 carbon atoms, and R² denotes hydrogen or alkyl or aryl having 1 to 12 carbon atoms).

A polyimide precursor comprising a structural unit represented by general formula (I) (in which A is a tetravalent aromatic group and B is a divalent aromatic group), wherein B in general formula (I) comprises a triazine moiety represented by the above formula (B1) (in which R¹ denotes hydrogen or alkyl or aryl having 1 to 12 carbon atoms, and R² denotes hydrogen or alkyl or aryl having 1 to 12 carbon atoms), and A in general formula (I) comprises a tetravalent residue obtainable by removing two carboxylic anhydride groups from 2,2-bis(3,4-dicarboxyphenyl)-1,1,1,3,3,3-hexafluoropropane dianhydride.

A polyimide precursor comprising a structural unit represented by general formula (I) (in which A is a tetravalent aliphatic group and B is a divalent aromatic group), wherein B in general formula (I) comprises a triazine moiety represented by following formula (B1) (in which R¹ denotes hydrogen or alkyl or aryl having 1 to 12 carbon atoms, and R² denotes hydrogen or alkyl or aryl having 1 to 12 carbon atoms).

A polyimide precursor in the above, wherein A in general formula (I) comprises a tetravalent residue obtainable by removing two carboxylic anhydride groups from at least one of cyclohexanetetracarboxylic dianhydride and 1,2,3,4-cyclobutanetetracarboxylic dianhydride.

2. A polyimide precursor according to the above item 1, wherein A in general formula (I) comprises a tetravalent residue obtainable by removing two carboxylic anhydride groups from 3,3',4,4'-biphenyltetracarboxylic dianhydride, pyromellitic dianhydride and 2,2-bis(3,4-dicarboxyphenyl)-1,1,1,3,3,3-hexafluoropropane dianhydride.

3. A polyimide precursor according to the above item 1, wherein A in general formula (I) comprises a tetravalent residue obtainable by removing two carboxylic anhydride groups from pyromellitic dianhydride.

4. A polyimide precursor according to the above item 1, wherein A in general formula (I) comprises a tetravalent residue obtainable by removing two carboxylic anhydride groups from 2,2-bis(3,4-dicarboxyphenyl)-1,1,1,3,3,3-hexafluoropropane dianhydride.

5. A polyimide precursor according to any one of the above items 1 to 4, wherein R¹ denotes hydrogen and R² denotes phenyl in general formula (B1).

6. A polyimide precursor according to any one of the above items 1 to 5, wherein B in general formula (I) comprises the triazine moiety represented by general formula (B1) in an amount of 10 to 100 mol %.

7. A polyimide obtainable from the polyimide precursor according to any one of items 1 to 6, comprising a structural unit represented by general formula (II):

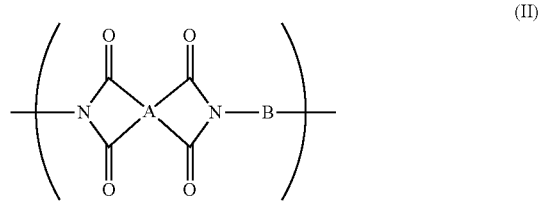

(II)

in which A and B are groups as defined in the above item 1.

8. A polyimide film comprising the polyimide according to the above item 7. A metal laminate comprising the polyimide film according to the above item 7 and metal layer laminated on the polyimide film directly or via an adhesive.

9. A method for producing 2,4-bis(3-aminoanilino)-6-substituted amino-1,3,5-triazine represented by general formula (B2), wherein the method comprising:

reacting 6-substituted amino-1,3,5-triazine-2,4-dihalide represented by general formula (B3) with 3-nitroaniline to form 2,4-bis-(3-nitroanilino)-6-substituted amino-1,3,5-triazine represented by general formula (B4), and reducing the obtained 2,4-bis-(3-nitroanilino)-6-substituted amino-1,3,5-triazine;

(B3)

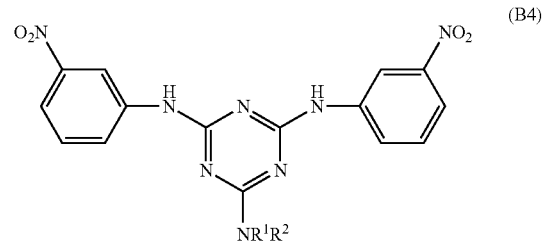

(B4)

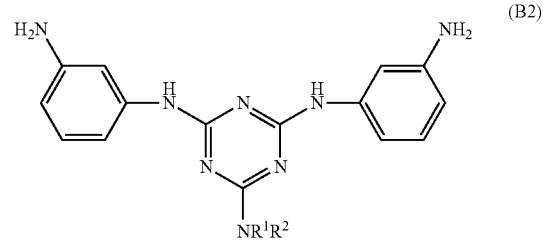

(B2)

(in which R¹ denotes hydrogen or alkyl or aryl having 1 to 12 carbon atoms, R² denotes hydrogen or alkyl or aryl having 1 to 12 carbon atoms, and X denotes halogen atom).

Effect of the Invention

According to the present invention, there is provided a polyimide film having excellent adhesiveness to metals and improved transmittance (improved transparency) in UV-visible range, and the method for producing a triazine compound used for manufacturing thereof.

In the present invention, the bonding position of the structure of general formula (B1) is meta-position on the benzene ring relative to two NH groups bonded to the triazine ring (hereinafter, the compound having this structure may be referred to as "m-ATDA"). It is revealed, as shown in examples, this structure improves transmittance at UV-visible range remarkably compared with a structure with para-position relative to NH group.

Figure 1:
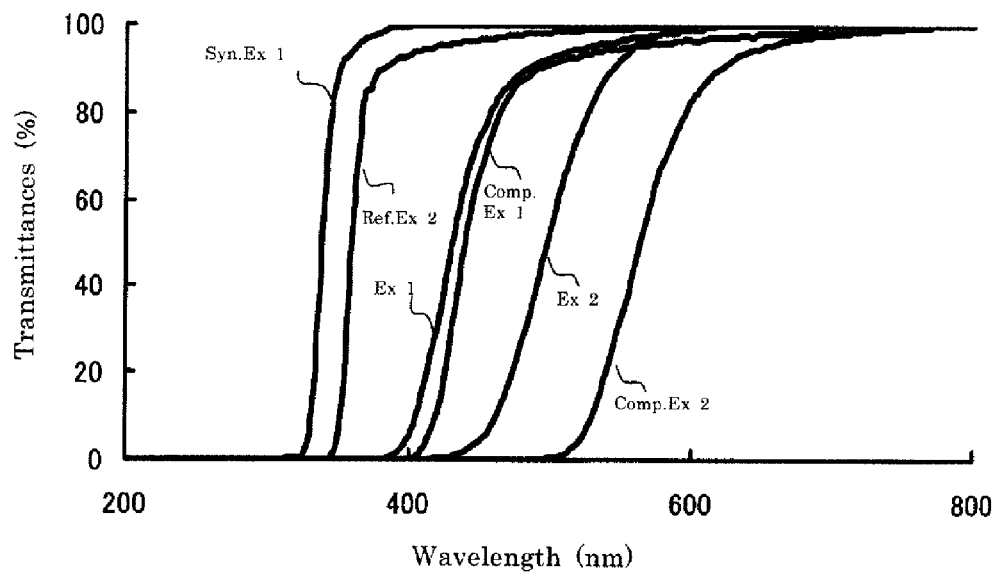
FIG. 1 shows UV-visible spectra of the triazine-based compounds and the polyimide films of the present invention.

In figures, Ex=Example, Syn.Ex=Synthesis Example, Comp. Ex=Comparative Example

EMBODIMENT FOR CARRYING OUT THE INVENTION

The polyimide precursor (polyamic acid) comprises a structural unit represented by general formula (I):

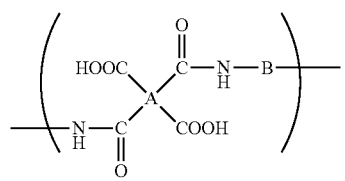

(I)

(in which A is a tetravalent aromatic group or aliphatic group and B is a divalent aromatic group). A is a residue obtainable by removing four COOH groups from tetracarboxylic acid (i.e. a residue obtainable by removing two carboxylic anhydride groups $(CO)_2O$ from tetracarboxylic dianhydride), and B is a residue obtainable removing two $NH_2$ groups from diamine.

The polyimide obtained from the polyimide precursor comprises a structural unit represented by general formula (II):

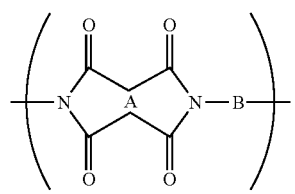

(II)

(in which A is a tetravalent aromatic group or aliphatic group and B is a divalent aromatic group). A is a residue obtainable by removing four COOH groups from tetracarboxylic acid (i.e. a residue obtainable by removing two carboxylic anhydride groups $(CO)_2O$ from tetracarboxylic dianhydride), and B is a residue obtainable removing two $NH_2$ groups from diamine. Hereinafter, tetracarboxylic acids and dianhydrides thereof and diamines used for the production of polyimides may be referred to as tetracarboxylic acid component and diamine component, respectively. A and B in general formulae (I) and (II) are contained in the polyimide structure originated from tetracarboxylic acid component and diamine component, respectively.

In the polyimide precursor and polyimide of the present invention, B in general formulae (I) and (II) comprises a triazine moiety represented by following formula (B1):

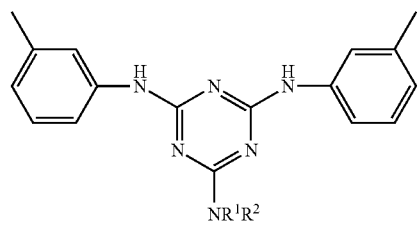

(B1)

(in which $R^1$ denotes hydrogen or alkyl or aryl having 1 to 12 carbon atoms, and $R^2$ denotes hydrogen or alkyl or aryl having 1 to 12 carbon atoms). For B in general formulae (I) and (II), the proportion of the group represented by formula (B1) is more than 0 to 100 mol %, preferably 5 to 100 mol % and further preferably 10 to 100 mol %.

Originated from 2,4-bis(3-aminoanilino)-6-substituted amino-1,3,5-triazine used as a diamine component, the structure of formula (B1) is introduced in the polyimide precursor and the polyimide. The details of the structure of formula (B1) will be clear from the description about diamine components described below.

The polyimide precursor of the present invention is preferably in the form of solution in view of handling properties. The polyimide of the present invention may be in the form of film, powder, solution and any other desired form, but the following explanation will be given to, as an example, a production of a polyimide film.

The polyimide film is obtained by thermal imidization and/or chemical imidization, and in case that plurality of tetracarboxylic acid components and/or diamine components are included, it may be a random copolymer or block copolymer, or combination of these.

The thickness of the polyimide film is not particularly limited, but it is 5 to 120 μm, preferably 6 to 75 μm, further preferably 7 to 60 μm.

Examples of a process for manufacturing a polyimide film generally include:

(1) a process comprising flow-casting, on a support in a form of film, a polyamic acid solution or a polyamic acid solution composition containing, as necessary, additives selected from an imidization catalyst, a dehydrating agent, a release assisting agent and inorganic fine particles in a polyamic acid solution, drying the film by heating to give a self-supporting film, and then heating it for cyclodehydration and for desolvation to give a polyimide film;

(2) a process comprising flow-casting, on a support in a form of film, a polyamic acid solution composition prepared by adding a cyclization catalyst and a dehydrating agent and a further selected additive, as necessary, such as inorganic fine particles to a polyamic acid solution; then chemically cyclodehydrating it and, as necessary, drying it by heating to give a self-supporting film, which is then heated for desolvation and imidization to give a polyimide film;

(3) when a polyimide is soluble in an organic solvent, a process comprising flow-casting, on a support in a form of film, a polyimide solution composition containing selected additives such as a release assisting agent and inorganic fine particles, drying by heating it to partially or completely remove a solvent, and then heating it to a maximum heating temperature to give a polyimide film: and (4) when a polyimide is soluble in an organic solvent, a process for producing a polyimide film by flow-casting, on a support in a form of film, a polyimide solution composition containing selected additives such as a release assisting agent and inorganic fine particles, heating the film to a maximum heating temperature while a solvent is removed, to give a polyimide film.

In the above production processes, the heating process after forming a self-supporting film is conducted at such a temperature that a maximum heating temperature is preferably 300° C. or higher, 350° C. or higher, further 450° C. or higher. This improves peeling strength after the heating process.

In the heating at a maximum heating temperature in the above production processes, the film may be heated on the support or heated after peeled from the support.

The polyimide film is preferably produced from a polyimide precursor (polyamic acid).

There will be described production processes and starting materials used for the polyimide precursor and the polyimide.

<Tetracarboxylic Acid Component and Diamine Component>

The tetracarboxylic acid dianhydride constituting the tetracarboxylic acid component may be an aromatic one or an aliphatic one.

The specific examples of aromatic tetracarboxylic dianhydrides include 3,3',4,4'-biphenyl tetracarboxylic dianhydride (s-BPDA) and pyromellitic dianhydride (PMDA), and in addition, 2,3,3',4'-biphenyl tetracarboxylic dianhydride (a-BPDA), oxydiphthalic dianhydride, diphenyl sulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride (6FDA), 2,3,3',4'-benzophenone tetracarboxylic dianhydride, 3,3',4,4'-benzophenone tetracarboxylic dianhydride, bis(3,4-dicarboxyphenyl)methane dianhydride, 2,2-bis(3,4-dicarboxyphenyl)propane dianhydride, p-phenylene bis(trimellitic acid monoester anhydride), p-biphenylene bis(trimellitic acid monoester anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy)benzene dianhydride, 1,4-bis(3,4-dicarboxyphenoxy)benzene dianhydride, 1,4-bis(3,4-dicarboxyphenoxy)biphenyl dianhydride, 2,2-bis[(3,4-dicarboxyphenoxy)phenyl]propane dianhydride, 2,3,6,7-naphthalene tetracarboxylic dianhydride, 1,4,5,8-naphthalene tetracarboxylic dianhydride, 4,4'-(2,2-hexafluoroisopropylidene)diphthalic dianhydride. These are used alone or in combination of two or more. The tetracarboxylic dianhydride used herein is suitably selected in consideration of desired properties and the like.

The tetracarboxylic acid component preferably comprises at least an acid dianhydride selected from s-BPDA, PMDA and 6FDA. Among them, PMDA is preferred. The use of PMDA provides high heat resistance of the polyimide film. In addition, it provides large difference between the transmittance at UV-visible range of the polyimide film in case m-ATDA is used as diamine component and the transmittance at UV-visible range of the polyimide film in case p-ATDA is used. In this embodiment, PMDA is preferably contained in an amount of 50 mol % or more, more preferably 70 mol % or more, particularly preferably 75 mol % or more, in 100 mol % of tetracarboxylic acid component.

In an embodiment of the present invention, it is also preferred to contain 6FDA as an tetracarboxylic acid component. When 6FDA is used, the solubility of a polyimide film to an organic solvent in the case m-ATDA is used as diamine component is higher than that in the case p-ATDA is used. In this embodiment, 6FDA is preferably contained in an amount of 50 mol % or more, more preferably 70 mol % or more, particularly preferably 75 mol % or more, in 100 mol % of tetracarboxylic acid component.

In an embodiment of the present invention, s-BPDA is preferably contained in an amount of 50 mol % or more, more preferably 70 mol % or more, particularly preferably 75 mol % or more, in 100 mol % of tetracarboxylic acid component. The polyimide film obtained using the tetracarboxylic acid component comprising s-BPDA in this amount provides a polyimide film having excellent mechanical properties.

As aliphatic tetracarboxylic dianhydrides, alicyclic tetracarboxylic dianhydrides are preferably used. When the aliphatic tetracarboxylic dianhydrides are combined with ATDA (m-ATDA, p-ATDA), the transmittance at UV-visible range is remarkably improved. The examples of the aliphatic tetracarboxylic dianhydrides include the following ones and their derivatives.

Cyclohexanetetracarboxylic dianhydrides (hereinafter it may be referred to as "CHDA"), such as (1S,2R,4S,5R)-cyclohexanetetracarboxylic dianhydride, (cis,cis,cis 1,2,4,5-cyclohexanetetracarboxylic dianhydride), (1S,2S,4R,5R)-cyclohexanetetracarboxylic dianhydride, (1R,2S,4S,5R)-Cyclohexanetetracarboxylic dianhydride; and bicyclo[2.2.2]octane-2,3,5,6-tetracarboxylic dianhydride, bicyclo[2.2.2]oct-7-ene-2,3,5,6-tetracarboxylic dianhydride, 4-(2,5-dioxo tetrahydrofuran-3-yl)-tetralin-1,2 dicarboxylic anhydride, tetrahydrofuran-2,3,4,5-tetracarboxylic dianhydride, bicyclo-3,3',4,4'-tetracarboxylic dianhydride, 1,2,3,4-cyclopentanetetracarboxylic dianhydride, 1,2,3,4-cyclobutanetetracarboxylic dianhydride (may be referred to as "CBDA"), 1,3-dimethyl-1,2,3,4-cyclobutanetetracarboxylic dianhydride, 1,4-dimethyl-1,2,3,4-cyclobutanetetracarboxylic dianhydride, 1,2,3,4-cyclohexanetetracarboxylic dianhydride, pentacyclo[8.2.1.1$^{4,7}$.0$^{2,9}$.0$^{3,8}$]tetradecane-5,6,11,12-tetracarboxylic dianhydride, 5-(2,5-dioxotetrahydrofuryl)-3-methyl-3-cyclohexene-1,2-dicarboxylic anhydride, cyclohexa-1-ene-2,3,5,6-tetracarboxylic dianhydride, and bicyclo[2.2.1]heptane-2,3,5,6-tetracarboxylic dianhydride.

These alicyclic tetracarboxylic dianhydrides may be used alone or in combination of two or more. The aliphatic tetracarboxylic dianhydride is preferably at least one of CHDA and CBDA.

The example and preferred structure of A in general formulae (I) and (II) correspond to the tetravalent residue obtainable by removing two carboxylic anhydride groups from the above tetracarboxylic dianhydrides, and the proportion thereof corresponds to the description of the above tetracarboxylic acid component.

The diamine component comprises a diamine compound represented by general formula (B2).

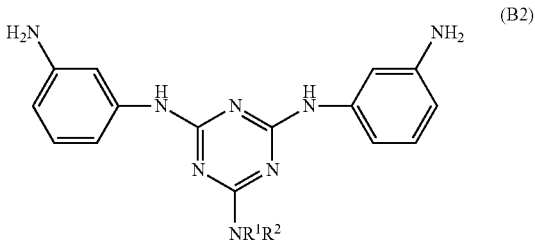

R$^1$ denotes hydrogen or alkyl or aryl having 1 to 12 carbon atoms (preferably 1 to 10 carbon atoms, more preferably 1 to 6 carbon atoms), and $R^2$ denotes hydrogen or alkyl or aryl having 1 to 12 carbon atoms (preferably 1 to 10 carbon atoms, more preferably 1 to 6 carbon atoms), and $R^1$ and $R^2$ may be different or the same.

The examples of alkyl group having 1 to 12 carbon atoms or an aryl group for $R^1$ and $R^2$ include methyl, ethyl, propyl, isopropyl, butyl, isobutyl, t-butyl, phenyl, benzyl, naphthyl, methylphenyl, biphenyl and the like.

In the diamine compound represented by general formula (B2), aminoanilino groups connected to two NH groups bonded to the triazine ring are 3-aminoanilino (mata-position). As described in examples, the transmittance (transparency) at UV-visible range of the obtained polyimide is improved remarkably compared with a compound having 4-aminoanilino (para-position).

The specific examples of diamine represented by general formula (I) include 2,4-bis(3-aminoanilino)-6-anilino-1,3,5-triazine, 2,4-bis(3-aminoanilino)-6-benzylamino-1,3,5-triazine, 2,4-bis(3-aminoanilino)-6-naphthylamino-1,3,5-triazine, 2,4-bis(3-aminoanilino)-6-biphenylamino-1,3,5-triazine, 2,4-bis(3-aminoanilino)-6-diphenylamino-1,3,5-triazine, 2,4-bis(3-aminoanilino)-6-dibenzylamino-1,3,5-triazine, 2,4-bis(3-aminoanilino)-6-dinaphthylamino-1,3,5-triazine, 2,4-bis(3-aminoanilino)-6-N-methylanilino-1,3,5-triazine, 2,4-bis(3-aminoanilino)-6-N-methylnaphthylamino-1,3,5-triazine, 2,4-bis(3-aminoanilino)-6-methylamino-1,3,5-triazine, 2,4-bis(3-aminoanilino)-6-ethylamino-1,3,5-triazine, 2,4-bis(3-aminoanilino)-6-dimethylamino-1,3,5-triazine, 2,4-bis(3-aminoanilino)-6-diethylamino-1,3,5-triazine, 2,4-bis(3-aminoanilino)-6-dibutylamino-1,3,5-triazine, 2,4-bis(3-aminoanilino)-6-amino-1,3,5-triazine.

The diamine component may comprise diamine compound(s) that is generally used in the production of polyimide in addition to the diamine compound represented by general formula (B2). The specific examples include:

1) diamines having one benzene ring, such as paraphenylene diamine(1,4-diaminobenzene; PPD), 1,3-diaminobenzene, 2,4-toluenediamine, 2,5-toluenediamine, 2,6-toluenediamine, 2) diamines having two benzene rings, for example diaminodiphenyl ethers, such as 4,4'-diaminodiphenyl ether (ODA), 3,3'-diaminodiphenyl ether, 3,4'-diaminodiphenyl ether; 4,4'-diaminodiphenyl methane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenyl methane, 3,3'-dicarboxy-4,4'-diaminodiphenyl methane, 3,3',5,5'-tetramethyl-4,4'-diaminodiphenyl methane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenyl sulfone, 3,4'-diaminodiphenyl sulfone, 4,4'-diaminodiphenyl sulfone, 3,3'-diaminobenzophenone, 3,3'-diamino-4,4'-dichlorobenzophenone, 3,3'-diamino-4,4'-dimethoxybenzophenone, 3,3'-diaminodiphenyl methane, 3,4'-diaminodiphenyl methane, 4,4'-diaminodiphenyl methane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide, 4,4'-diaminodiphenyl sulfoxide, 3) diamines having three benzene rings, for example, 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenylsulfide)benzene, 1,3-bis(4-aminophenylsulfide)benzene, 1,4-bis(4-aminophenylsulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene, 1,4-bis[2-(4-aminophenyl)isopropyl]benzene, 4) diamines having four benzene rings, for example, 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl]ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy)phenyl]ketone, bis[3-(3-aminophenoxy)phenyl]sulfide, bis[3-(4-aminophenoxy)phenyl]sulfide, bis[4-(3-aminophenoxy)phenyl]sulfide, bis[4-(4-aminophenoxy)phenyl]sulfide, bis[3-(3-aminophenoxy)phenyl]sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane, 2,2-bis[4-(4-aminophenoxy)phenyl]-1,1,1,3,3,3-hexafluoropropane.

These are used alone or in combination of two or more. The diamine used herein is suitably selected in consideration of desired properties and the like.

The diamine component may comprise diamine compound represented by general formula (C) (p-ATDA) that is a para-isomer of the compound represented by general formula (B2).

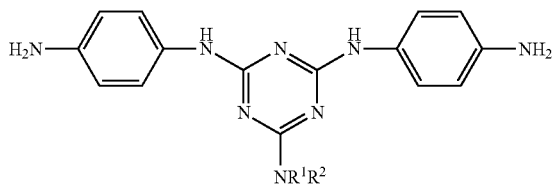

(C)

(in which $R^1$ and $R^2$ denote the same meaning defined for formula (B2))

In the present invention, the diamine compound represented by general formula (B2) is used in amount of more than 0 to 100 mol % or less, preferably 5 to 100 mol % and further preferably 10 to 100 mol %, and preferably 15 to 100 mol % and more preferably 17 to 100 mol %, and in a specific embodiment 25 to 100 mol % based on the total diamine component (=100 mol %).

When diamine(s) other than the diamine compound represented by formula (B2) is used, the diamine component comprises diamine compound preferably selected from paraphenylene diamine (PPD) and diaminodiphenyl ethers, more preferably one or more compound selected from PPD, 4,4'-diaminodiphenyl ether and 3,4'-diaminodiphenyl ether, and particularly preferably PPD. The polyimide film obtained from these is excellent in mechanical property and the like.

The example and preferred structure of B in general formula (I) correspond to the divalent residue obtainable by removing $NH_2$ from the above diamines, and the proportion thereof corresponds to the description of the above diamine component.

A polyimide of the present invention is preferably free from at least one proton-conducting functional group selected from the group consisting of —$SO_3H$, —COOH and —$PO_3H_2$ as described in Patent Document 5, for excellent heat resistance.

<Preparation of a Polyimide Precursor>

A polyimide precursor (polyamic acid) is produced by reacting a tetracarboxylic acid component and a diamine component in a known manner; for example, substantially equimolar components may be reacted in an organic solvent to give a solution of a polyamic acid (partial imidization may be allowed to take place if the solution is maintained in homogeneous state). Alternatively, two or more polyamic acids in which one of the components is relatively excessively contained are preliminarily synthesized, and these polyamic acid solutions can be combined and mixed under the reaction conditions. The polyamic acid solution thus prepared can be used for production of a self-supporting film as it is or, as necessary, after removing or adding a solvent.

When a polyimide obtained is soluble in an organic solvent, the polyimide can be obtained by reacting a tetracarboxylic acid component and a diamine component in a known manner. For example, a polyimide solution can be produced by reacting substantially equimolar components in an organic solvent. Alternatively, two or more polyimides in which one of the components is relatively excessively contained are preliminarily synthesized, and these polyimide solutions can be combined and mixed under the reaction conditions.

An organic solvent used herein for the polyamic acid solution or polyimide solution can be a known solvent such as N-methyl-2-pyrrolidone (NMP), N,N-dimethylformamide, N,N-dimethylacetamide (DMAc) and N,N-diethylacetamide. These organic solvents are used alone or in combination of two or more.

In the polymerization reaction of a polyamic acid and a polyimide, a concentration of the total monomers in an organic polar solvent can be appropriately selected depending on an intended use; for example, a concentration of the total monomers in an organic polar solvent is preferably 5% by mass to 30% by mass, further preferably 15% by mass to 27% by mass, particularly preferably 18% by mass to 26% by mass.

As an example of a process for preparing a polyamic acid, the above polymerization reaction of an aromatic tetracarboxylic acid component and an aromatic diamine component is conducted, for example, by mixing them in substantially equimolar amounts or in amounts such that one of them is slightly in excess of the other component (the acid component or the diamine component) and reacting them at a reaction temperature of 100° C. or lower, preferably 80° C. or lower for about 0.2 to 60 hours to give a polyamic acid solution.

As an example of a process for preparing a polyimide, the above polymerization reaction of an aromatic tetracarboxylic acid component and an aromatic diamine component is conducted, for example, by mixing them in substantially equimolar amounts or in amounts such that one of them is slightly in excess of the other component (the acid component or the diamine component) and processed by a known method to give a polyimide solution; for example, the mixture can be reacted at a reaction temperature of 140° C. or higher, preferably 160° C. or higher (preferably 250° C. or lower, further preferably 230° C. or lower) for about 1 to 60 hours to give a polyimide solution.

For thermal imidization, the polyamic acid solution may contain, as necessary, an imidization catalyst, an organic phosphorous-containing compound, inorganic fine particles or the like. For chemical imidization, the polyamic acid solution may contain, as necessary, a cyclization catalyst, a dehydrating agent, inorganic fine particles or the like. The polyimide solution may contain an organic phosphorous-containing compound, inorganic fine particles or the like. Furthermore, inorganic fine particles may be replaced by polyimide fine particles insoluble in an organic solvent.

Examples of an imidization catalyst include substituted or unsubstituted nitrogen-containing heterocyclic compounds, N-oxide compounds of the nitrogen-containing heterocyclic compounds, substituted or unsubstituted amino acid compounds, hydroxy-containing aromatic hydrocarbon compounds or aromatic heterocyclic compounds. Particularly preferably used is lower-alkylimidazoles such as 1,2-dimethylimidazole, N-methylimidazole, N-benzyl-2-methylimidazole, 2-methylimidazole, 2-ethyl-4-methylimidazole and 5-methylbenzimidazole; benzimidazoles such as N-benzyl-2-methylimidazole; isoquinoline; and substituted pyridines such as 3,5-dimethylpyridine, 3,4-dimethylpyridine, 2,5-dimethylpyridine, 2,4-dimethylpyridine and 4-n-propylpyridine. The amount of the imidization catalyst is preferably about 0.01 to 2 equivalents, particularly preferably about 0.02 to 1 equivalents based on amide acid units in a polyamide acid. The use of an imidization catalyst sometimes improves physical properties of a polyimide film obtained, particularly elongation and edge-break resistance.

Examples of an organic phosphorous-containing compound include phosphoric esters such as monocaproyl phosphoric ester, monooctyl phosphoric ester, monolauryl phosphoric ester, monomyristyl phosphoric ester, monocetyl phosphoric ester, monostearyl phosphoric ester, tirethyleneglycol monotridecyl ether monophosphoric ester, tetraethyleneglycol monolauryl ether monophosphoric ester, diethyleneglycol monostearyl ether monophosphoric ester, dicaproyl phosphoric ester, dioctyl phosphoric ester, dicapryl phosphoric ester, dilauryl phosphoric ester, dimyristyl phosphoric ester, dicetyl phosphoric ester, distearyl phosphoric ester, tetraethyleneglycol mononeopentyl ether diphosphoric ester, triethyleneglycol monotridecyl ether diphosphoric ester, tetraethyleneglycol monolauryl ether diphosphoric ester and diethyleneglycol monostearyl ether diphosphoric ester and amine salts of these phosphoric esters. Examples of an amine include ammonia, monomethylamine, monoethylamine, monopropylamine, monobutylamine, dimethylamine, diethylamine, dipropylamine, dibutylamine, trimethylamine, triethylamine, tripropylamine, tributylamine, monoethanolamine, diethanolamine and triethanolamine.

Examples of a cyclization catalyst include aliphatic tertiary amines such as trimethylamine and triethylenediamine; aromatic tertiary amines such as dimethylaniline; and heterocyclic tertiary amines such as isoquinoline, pyridine, α-picoline and β-picoline.

Examples of a dehydrating agent include aliphatic carboxylic anhydrides such as acetic anhydride, propionic anhydride and butyric anhydride; and aromatic carboxylic anhydrides such as benzoic anhydride.

Examples of inorganic fine particles include inorganic oxide powders such as fine-particulate titanium dioxide powder, silicon dioxide (silica) powder, magnesium oxide powder, aluminum oxide (alumina) powder and zinc oxide powder; inorganic nitride powders such as fine-particulate silicon nitride powder and titanium nitride powder; inorganic carbide powders such as silicon carbide powder; and inorganic salt powders such as fine-particulate calcium carbonate powder, calcium sulfate powder and barium sulfate powder. These inorganic fine particles may be used in combination of two or more. For homogeneously dispersing these inorganic fine particles, a means known per se can be applied.

<Production of a Self-Supporting Film from a Polyamic Acid Solution>

A self-supporting film from a polyamic acid solution is produced by applying a polyamic acid solution on a support by flow casting and then heating it to such an extent that it becomes self-supporting state (it means it is in a stage before a usual curing process), for example, heating to such an extent that it can be peeled from the support.

There are no particular restrictions to a solid concentration of the polyamic acid solution as long as a viscosity is within the range suitable for the production, but generally, it is preferably 5 to 30% by mass, further preferably 15 to 27% by mass, and particularly preferably 18 to 26% by mass.

A temperature and duration of heating in producing a self-supporting film is determined as appropriate. For thermal imidization, heating is conducted, for example, at a temperature of 50 to 180° C. for about 1 to 60 min.

There are no particular restrictions to a support as long as a polyamic acid solution can be cast on it, but it is preferably a smooth substrate; for example, a glass plate or a metal (for example, stainless steel) drum or belt.

There are no particular restrictions to the self-supporting film as long as a solvent has been removed such that the film can be peeled from a support and/or it is imidized, but in thermal imidization, a weight-loss-after-heating is preferably within the range of 20 to 50% by mass and when a weight-loss-after-heating is within the range of 20 to 50% by mass and an imidization rate is within the range of 7 to 55%, a self-supporting film has satisfactory mechanical properties.

Here, a weight-loss-after-heating of a self-supporting film is determined in accordance with the following equation from a mass of the self-supporting film (W1) and the mass of a cured film (W2).

$$\text{Weight-loss-after-heating (\% by mass)} = \{(W1-W2)/W1\} \times 100$$

An imidization rate of the partially imidized self-supporting film is calculated by taking IR spectra of the self-supporting film and its fully-cured product (polyimide film) by the ATR method and determining an area or height of a vibrational band peak. A vibrational band peak employed can be, for example, a symmetric stretching vibration band of an imidocarbonyl group or a stretching vibration band of a benzene ring. More specifically, FT-IR spectra of a self-supporting film and its fully-cured film (polyimide film) were taken by the multireflection ATR method with Ge crystal and an incident angle of 45° using FT/IR6100 from JASCO Corporation, and an imidization rate was calculated in accordance with the following equation (1) using a ratio of a peak height of asymmetric stretching vibration of imidocarbonyl group at 1775 $cm^{-1}$ to a peak height of carbon-carbon symmetric stretching vibration of an aromatic ring at 1515 $cm^{-1}$.

$$\text{Imidization rate (\%)} = \{(X1/X2)/(Y1/Y2)\} \times 100 \qquad (1)$$

wherein

X1: peak height of a self-supporting film at 1775 $cm^{-1}$,
X2: peak height of a self-supporting film at 1515 $cm^{-1}$,
Y1: peak height of a fully-cured film at 1775 $cm^{-1}$,
Y2: peak height of a fully-cured film at 1515 $cm^{-1}$.

<Heating (Imidization) Process>

Subsequently, the self-supporting film is heated to give a polyimide film. The heating is conducted such that the maximum temperature is preferably 300° C. or higher, 350° C. or higher, more preferably 450° C. or higher, further preferably 470° C. or higher. There are no particular restrictions to the upper limit of the heating temperature as long as the properties of a polyimide film are not deteriorated; the temperature is preferably 600° C. or lower, more preferably 550° C. or lower, further preferably 530° C. or lower, most preferably 520° C. or lower.

One example of the heating process is the following manner. The heating is first conducted at a temperature of about 100° C. to lower than 350° C. for gradually imidizing the polymer and evaporating/removing the solvent over about 0.05 to 5 hours, particularly 0.1 to 3 hours. Particularly, the heating is preferably conducted stepwise, that is, the first heating at a relatively lower temperature of about 100° C. to about 170° C. for about 0.5 to 30 min, then the second heating at a temperature of higher than 170° C. and 220° C. or lower for about 0.5 to 30 min, then the third heating at an elevated temperature of higher than 220° C. and lower than 350° C. for about 0.5 to 30 min. Furthermore, it is preferable to conduct the fourth heating at a high temperature of 350° C. or higher and 600° C. or lower. The heating process can be conducted sequentially or continuously.

Heating (imidization) process of the self-supporting film may be carried out on the support or after peeled from the support. In heating in an industrial production, a long self-supporting film may be fixed at least at both edges in a direction perpendicular to its longitudinal direction, that is, in a width direction of the film by a fixing means such as pin tenters, clips and a frame in a cure furnace while the film is, if necessary, extended or contracted either in a width direction or in a longitudinal direction.

Then, the polyimide film of the present invention produced as described above may be further processed by, for example, sandblasting, corona treatment, plasma treatment or etching.

<Polyimide Laminate and Polyimide-Metal Laminate>

A polyimide film of the present invention has excellent adhesiveness to substrates such as a metal foil or materials such as an adhesive. Thus, there will be formed a polyimide laminate in which the polyimide film of the present invention and an adhesive layer are laminated, or a polyimide-metal laminate described later. Herein, copper is a preferred metal.

The examples of methods of producing a polyimide-metal laminate include methods of (1) laminating a polyimide film and a base material (for example, metal foil) directly or via an adhesive by compressing or heat-compressing, (2) forming a metal layer directly on a polyimide film by wet method (plating) or dry method (metalizing such as vacuum deposition or sputtering) and (3) coating a base material, such as metal foil, with the above mentioned polyamic acid solution or the polyimide solution and drying and imidizing (drying in case of polyimide solution).

As described above, a polyimide film, a polyimide-metal laminate (including both a laminate where a film and a metal layer are laminated via an adhesive layer and a laminate where a metal layer is directly formed on a film) and a polyimide laminate of the present invention may be used as a material for electronic components and an electronic devices including a printed-wiring board, a flexible printed board, a TAB tape, a COF tape or a metal wiring, or a cover substrate for a metal wiring and a chip member such as an IC chip and a base substrate for a liquid crystal display, an organic electroluminescence display, an electronic paper, a solar battery and the like.

The polyimide film of the present invention has excellent adhesiveness to a metal and improved transmittance at UV-visible range. Therefore, the polyimide is suitably used in a plastic substrate as a replacement for the glass substrate of, in particular, a display device such as a liquid crystal display, an EL display, or electronic paper.

<Polyimide Precursor, Polyimide and Polyimide Film Obtained Using Alicyclic Tetracarboxylic Dianhydride and ATDA (p-ATDA and m-ATDA)>

A polyimide precursor is obtained from alicyclic tetracarboxylic dianhydride and ATDA. A polyimide and a polyimide film are obtained from the polyimide precursor. The polyimide film has an excellent adhesiveness with base materials such as a metal foil or materials such as an adhesive. In addition, the polyimide film has an improved transmittance (transparency) at UV-visible range.

The alicyclic tetracarboxylic dianhydride and ATDA (p-ATDA and m-ATDA) are the same as those described in <Tetracarboxylic acid component and diamine component>. In addition, the method obtaining the polyimide precursor using the alicyclic tetracarboxylic dianhydride and ATDA (p-ATDA and m-ATDA) is the same as those described in <Preparation of a polyimide precursor>.

Further, the methods of obtaining the polyimide and polyimide film using the polyimide precursor are the same as those described in <Heating (imidization) process>.

Further, the methods of obtaining the polyimide laminate and polyimide-metal laminate using the polyimide film are the same as those described in <Polyimide laminate and Polyimide-metal laminate>.

<Method for Producing Compound of General Formula (B2)>

Next, a method for producing 2,4-bis(3-aminoanilino)-6-substituted amino-1,3,5-triazine represented by general formula (B2) that is used for the production of the polyimide of the present invention will be described.

First, 6-substituted amino-1,3,5-triazine-2,4-dihalide represented by general formula (B3) is prepared by reacting a cyanuric halide with an amino compound (NHR$^1$R$^2$) as shown in the following reaction scheme.

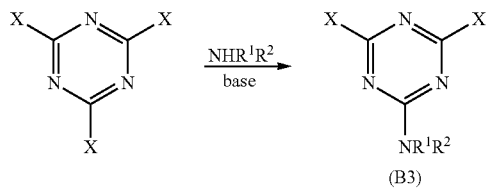

In the formula, X is halogen atom, preferably Cl, Br or I. As for R$^1$ and R$^2$, as defined for general formula (B2), R$^1$ denotes hydrogen or alkyl or aryl having 1 to 12 carbon atoms, R$^2$ denotes hydrogen or alkyl or aryl having 1 to 12 carbon atoms, and the preferred one is as mentioned for general formula (B2). The specific examples of R$^1$ and R$^2$ are those that the specific examples of general formula (B2) have.

Then, as shown in the following scheme, 6-substituted amino-1,3,5-triazine-2,4-dihalide represented by general formula (B3) is reacted with 3-nitroaniline to form 2,4-bis-(3-nitroanilino)-6-substituted amino-1,3,5-triazine represented by general formula (B4).

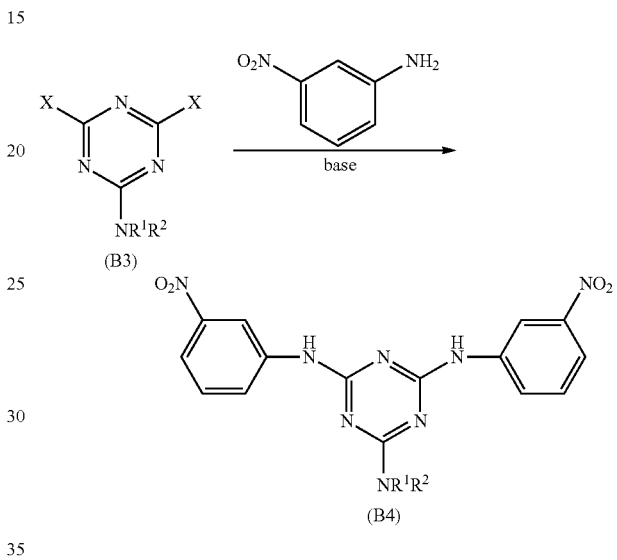

In the formula, X, R$^1$ and R$^2$ are the same as those mentioned above.

The above two reactions are preferably carried out in the presence of a base in a solvent. The base used herein is not particularly limited, and general inorganic base may be used, for example, sodium carbonate and the like.

Also, the solvent used herein is not particularly limited, but general solvents may be used, for example, ether-based solvents such as dioxane, tetrahydrofuran and diethyl ether; hydrocarbon-based solvent such as toluene and benzene; and amide-based solvents such as N,N-dimethylformamide, N,N-dimethylacetamide and N-methyl-2-pyrrolidone.

Then, 2,4-bis-(3-nitroanilino)-6-substituted amino-1,3,5-triazine represented by general formula (B4) thus obtained is reduced to convert nitro groups to amino groups, thereby producing 2,4-bis(3-aminoanilino)-6-substituted amino-1,3,5-triazine (B2).

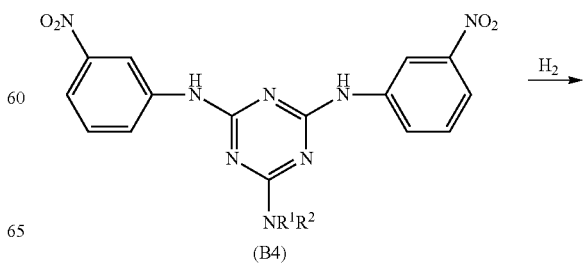

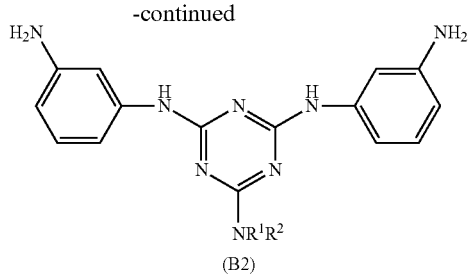

(B2)

Any known reduction method may be used as the reduction reaction. For example, it may be carried out by hydrogenation in a solvent with suitably heating and for example, in the presence of suitable catalyst. As the catalyst, any known one may be used such as palladium supported on carbon and the like.

The method for producing the 2,4-bis(3-aminoanilino)-6-substituted amino-1,3,5-triazine of the present invention is a novel method. The details of the reaction will be described in examples, but a person skilled in the art can modify the solvent, feeding amount, reaction condition and the like, and may perform a post treating process, purification and the like according to conventional methods.

The inventors of the present invention confirmed that 2,4-bis(4-aminoanilino)-6-substituted amino-1,3,5-triazine was obtained by reacting 6-substituted amino-1,3,5-triazine-2,4-dihalide (B3) with excessive amount of para-phenylenediamine. Then, the inventors tried to obtain 2,4-bis(3-aminoanilino)-6-substituted amino-1,3,5-triazine by reacting 6-substituted amino-1,3,5-triazine-2,4-dihalide (B3) with excessive amount of meta-phenylenediamine. However, the inventors failed to obtain m-ATDA.

According to the production method of the present invention, 2,4-bis(3-aminoanilino)-6-substituted amino-1,3,5-triazine (B2) can be obtained in high yield.

EXAMPLES

The present invention will be further explained in details with reference to examples, but the present invention is by no means limited to these examples.
<Method of Evaluation>
Evaluation of the properties of polyamic acids and polyimides was carried out based on the following methods.

(1) Measurement of Logarithmic Viscosity Number of Polyamic Acid

A polyamic acid solution prepared as described below was diluted to 0.5 g/dL with N,N-dimethylacetamide, and its logarithmic viscosity number was determined using an Ostwald's viscometer at 30° C.

(2) Solubility Test of Polyimide Films 10 mg of the obtained polyimide film was added in 5 mL of an organic solvent. "++" was recorded when it dissolved at room temperature, "+" was recorded when it dissolved at room temperature after heating, "±" was recorded when it partially dissolved or swelled, and "−" was recorded when it was insoluble. The organic solvents used were DMAc, NMP, THF and chloroform.

(3) Measurement of Logarithmic Viscosity Number of Polyimide Solution

The obtained polyimide was dissolved in N-methyl-2-pyrrolidone (NMP) to give a concentration of 0.5 g/dL, and its logarithmic viscosity number was determined using an Ostwald's viscometer at 30° C.

(4) Glass Transition Temperature

A glass transition temperature was determined by DSC-60 manufactured by Shimadzu Corporation at a rate of temperature increase of 20° C./min under nitrogen.

(5) Coefficient of Liner Thermal Expansion of Polyimide Film

Measurement was carried out by EXSTAR TMA/SS6100 manufactured by Seiko Instruments Inc. (rate of temperature increase: 10° C./min), and coefficient of liner thermal expansion was determined.

(6) Optical Property
Diamine Monomer

UV-visible spectra of m-ATDA and p-ATDA were measured for $1 \times 10^{-5}$ mol/L in tetrahydrofuran solution by V-570 UV-visible spectroscope manufactured by JASCO Corporation. Cut-off wavelength "$\lambda_{cutoff}$" and 80%-transmittance wavelength "$\lambda_{80\%}$" were determined. Transmittances at wavelength of 400, 500 and 600 nm were determined.

Polyimide Film

UV-visible spectra of polyimide films obtained as described later were measured by V-570 UV-visible spectroscope manufactured by JASCO Corporation. Cut-off wavelength "$\lambda_{cutoff}$" and 80%-transmittance wavelength "$\lambda_{80\%}$" were determined. Transmittances at wavelength of 400, 500 and 600 nm were determined.

(7) Refractive Index of Polyimide Film

Refractive Index at D line (589 nm) of polyimide film was measured at room temperature by Abbe refractometer DR-M4 manufactured by Atago Co., Ltd.

(8) Measurement of Peel Strength of Polyimide-Metal Laminate

90°-peel strength for the obtained polyimide-metal laminate was measured at a peel rate of 50 mm/min under the environment at temperature of 23° C. and relative humidity of 50%.

Synthesis Referential Example 1

Synthesis of 6-anilino-1,3,5-triazine-2,4-dichloride (ATD)

Into a three neck flask (1 L) equipped with a stirrer, a thermometer, a dropping funnel and a calcium chloride tube, cyanuric chloride (36.52 g, 0.2 mol) and THF (120 mL) were charged and dissolved completely with cooling at −5° C. to 0° C. with an ice bath. To the three neck flask, a solution of aniline (19.03 g, 0.2 mol) dissolved in THF (70 mL) was added dropwise gradually. After the dropwise addition, the mixture was stirred for 2 hours at 0° C. to 5° C. To the three neck flask, a solution of sodium carbonate (12.90 g, 0.12 mol) dissolved in distilled water (70 mL) was added dropwise gradually with taking care not to raise the temperature of the mixture. After the dropwise addition, the mixture was stirred for 2 hours. The reaction mixture was fed into a separating funnel, and saturated saline solution was added. Anhydrous magnesium sulfate was added in the separated organic phase, and the mixture was stirred overnight. After removing the anhydrous magnesium sulfate by suction filtration, THF was evaporated by an evaporator to obtain a solid crude product. The crude product was recrystallized from dehydrated hexane/toluene mixed solvent to obtain white needle-like crystal.

Yield (quantity): 40.6 g, Yield (ratio): 84%, Melting point: 136-137° C.

$^1$H-NMR [400 MHz, DMSO-$d_6$, ppm]: δ 7.18 (t, 1H, Ar—H), 7.40 (t, 2H, Ar—H), 7.61 (d, 2H, Ar—H), 8.92 (s, 1H, NH)

$^{13}$C NMR [101 MHz, DMSO-d$_6$, TMS, ppm]: δ 170.1, 169.2, 164.2, 137.3, 129.3, 125.4, 122.0

Synthesis Referential Example 2

Synthesis of 2,4-bis(4-aminoanilino)-6-anilino-1,3,5-triazine (p-ATDA)

Synthesis of Comparative Diamine Compound

Into a three neck flask (1 L) equipped with a stirrer, a condenser, a dropping funnel with side-tube and a nitrogen inlet, 1,4-dioxane (100 mL), sodium carbonate (8.90 g, 0.08 mol), p-phenylenediamine (34.62 g, 0.32 mol) were charged and dissolved by heating. 6-anilino-1,3,5-triazine-2,4-dichloride (10.11 g, 0.04 mol) dissolved in 1,4-dioxane (80 mL) was charged in the dropping funnel, and added dropwise taking 5 hours into the refluxing solution. The mixture was stirred overnight at the refluxing temperature. After the reaction, the reaction mixture was washed in a beaker (3 L) four times with hot water, once with water so that the washed water became transparent. The solid was collected by suction filtration, and the solid was added in acetone and dissolved by stirring for 30 min at refluxing temperature, and insoluble matters were filtered off. Acetone was removed from the filtrate by evaporator to obtain a crude product. The crude product was recrystallized from hexane/toluene. Herein, active carbon-treatment was carried out by adding active carbon and refluxing for about one hour before the hot-filtration. Then, the crystal obtained after the hot-filtration was dried in vacuo for 6 hours at 190° C. Light brown powder was obtained.

Yield (quantity): 9.17 g, Yield (ratio): 58%, Melting point: 224-225° C.

$^1$H-NMR [400 MHz, DMSO-d$_6$, TMS, ppm]: δ 4.78 (s, 4H, Ar—NH$_2$), 6.53 (d, 4H, NH$_2$-o-Ar—H), 6.94 (t, 1H, p-Ar—H), 7.23 (t, 2H, m-Ar—H), 7.34 (d, 4H, NH$_2$-m-Ar—H), 7.79 (d, 2H, o-Ar—H), 8.64 (s, 2H, Ar—NH—Ar), 8.95 (s, 1H, Ar—NH)

$^{13}$C NMR [101 MHz, DMSO-d$_6$, TMS, ppm]: δ 164.1, 164.0, 144.1, 140.4, 129.0, 128.2, 122.6, 121.4, 119.9, 113.8

Elemental Analysis (C$_{21}$H$_{20}$N$_8$ Mw: 384.44)
Calculated value (%) C, 65.61; H, 5.24; N, 29.15
Measured value (%) C, 65.88; H, 5.36; N, 29.07

Synthesis Example 1

(i) Synthesis of 2,4-bis(3-nitroanilino)-6-anilino-1,3,5-triazine (NAT)

Synthesis of Compound of General Formula (B4)

Into a three neck flask (1 L) equipped with a stirrer, a condenser, a dropping funnel with side-tube and a nitrogen inlet, 6-anilino-1,3,5-triazine-2,4-dichloride (15.0 g, 0.062 mol), 3-nitroaniline (10.27 g, 0.074 mol), sodium carbonate (4.32 g, 0.041 mol) and 1,4-dioxane (150 mL) were charged and heated to a reflux temperature and stirred overnight while maintaining the temperature. Then, the mixture was poured into an excessive amount of water, suction-filtered, washed with methanol and recrystallized from dioxane/hexane. After dried in vacuo for 8 hours at 130° C., light yellow powder crystal was obtained.

Yield (quantity): 14.6 g, Yield (ratio): 53%, Melting point: 217-218° C.

$^1$H-NMR [400 MHz, DMSO-d$_6$, TMS, ppm]: δ 7.04 (t, 1H, Ar—H), 7.31 (t, 2H, Ar—H), 7.59 (t, 2H, Ar—H), 7.78 (d, 2H, Ar—H), 7.84 (d, 2H, Ar—H), 8.29 (s, 2H, Ar—H), 8.61 (s, 2H, Ar—H), 9.48 (s, 1H, NH), 9.84 (s, 2H, NH)

$^{13}$C NMR [101 MHz, DMSO-d$_6$, ppm]: d=164.9, 164.5, 148.5, 141.5, 139.9, 130.2, 128.9, 126.7, 123.0, 121.2, 117.0, 114.8

Elemental Analysis (C$_{21}$H$_{16}$N$_8$O$_4$)
Calculated value (%) C, 56.76; H, 3.63; N, 25.21
Measured value (%) C, 56.98; H, 3.72; N, 25.08

(ii) Synthesis of 2,4-bis(3-aminoanilino)-6-anilino-1,3,5-triazine (m-ATDA)

Synthesis of Compound of General Formula (B2)

Into a three neck flask (1 L) equipped with a three-way cock, a pressure-resistant balloon filled with hydrogen and a condenser, 2,4-bis(3-nitroanilino)-6-anilino-1,3,5-triazine (10.00 g, 0.023 mol) and DMAc (250 mL) were added, and further 5 wt % Pd/C (0.53 g) was added and stirred. The operation of filling hydrogen in the flask and deairation by an aspirator was repeated three times, and hydrogen was filled in the flask. Then, the mixture was stirred for 72 hours at 80° C. After the reaction, Pd/C was filtered off by suction filtration, and DMAc was removed from the filtrate to obtain solid crude product. This was dissolved in THF and active carbon treatment was carried out for 30 min at refluxing temperature. Active carbon was removed by filtration and THF was removed from the filtrate to obtain white solid product. The recrystallization was carried out from dioxane/hexane and dried in vacuo for 7 hours at 170° C. White powder crystal was obtained.

Yield (quantity): 4.58 g, Yield (ratio): 53%, Melting point: 186-187° C.

$^1$H-NMR [400 MHz, DMSO-d$_6$, ppm]: δ=4.92 (s, 4H, NH$_2$), 6.26 (s, 1H, Ar—H), 6.96 (t, 2H, Ar—H), 7.00 (d, 2H, Ar—H), 7.05 (t, 1H, Ar—H), 7.28 (s, 2H, Ar—H), 7.31 (t, 2H, Ar—H), 7.82 (t, 2H, Ar—H), 8.88 (s, 2H, NH), 9.05 (s, 1H, NH)

$^{13}$C NMR [101 MHz, DMSO-d$_6$, ppm]: d=164.1, 164.0, 148.6, 140.3, 140.1, 128.5, 121.7, 120.0, 109.0, 108.5, 106.7

Elemental Analysis (C$_{21}$H$_{20}$N$_8$)
Calculated value (%) C, 65.61; H, 5.24; N, 29.15
Measured value (%) C, 65.42; H, 5.35; N, 29.31

Synthesis Comparative Example 1

Into a three neck flask (1 L) equipped with a stirrer, a condenser, a dropping funnel with side-tube and a nitrogen inlet, 1,4-dioxane (100 mL), sodium carbonate (8.90 g, 0.08 mol) and meta-phenylenediamine (34.62 g, 0.32 mol) was charged and dissolved by stirring at reflux temperature. 6-anilino-1,3,5-triazine-2,4-dichloride (10.11 g, 0.04 mol) dissolved in 1,4-dioxane (80 mL) was charged in the dropping funnel, and added dropwise taking 5 hours into the refluxing solution. The mixture was stirred overnight at the refluxing temperature. After the reaction, the reaction mixture was washed in a beaker (3 L) four times with hot water, once with water so that the washed water became transparent. The solid was collected by suction filtration, and stirred for 30 min in acetone at refluxing temperature, and insoluble matters were filtered off. Acetone was removed from the filtrate by evaporator to obtain a solid matter. The recrystallization of the solid matter was tried from 1,4-dioxane/hexane. However, the crystal of the product (m-ATDA) was not obtained.

Next, polyamic acid solutions were prepared.

(Preparation of Polyamic Acid Solution A)
s-BPDA/p-ATDA

Into a three neck flask (100 mL) equipped with a stirring rod and a nitrogen inlet, 2,4-bis(4-aminoanilino)-6-anilino-1,3,5-triazine (p-ATDA) (0.961 g, 2.50 mmol) and N,N-dimethylacetamide (DMAc) (5 mL) were charged and dissolved by stirring at room temperature. Then, to the mixture, 3,3',4,4'-biphenyltetracarboxylic dianhydride (s-BPDA) (0.736 g, 2.50 mmol) was added and reacted at room temperature with stirring for 6 hours to obtain a viscous polymerization solution, which was diluted with DMAc, giving polyamic acid solution A (polyimide precursor solution A). Logarithmic viscosity number ($\eta_{inh}$) of the polyamic acid was 1.29 dL/g.

(Preparation of Polyamic Acid Solution B)
s-BPDA/m-ATDA

Polyamic acid solution B was prepared in a similar manner to the preparation of polyamic acid solution A except that 2,4-bis(3-aminoanilino)-6-anilino-1,3,5-triazine (m-ATDA) was used as a diamine. Logarithmic viscosity number ($\eta_{inh}$) of the polyamic acid was 1.20 dL/g.

(Preparation of Polyamic Acid Solution C)
PMDA/p-ATDA

Polyamic acid solution C was prepared in a similar manner to the preparation of polyamic acid solution A except that pyromellitic dianhydride (PMDA) was used as an acid dianhydride. Logarithmic viscosity number ($\eta_{inh}$) of the polyamic acid was 0.38 dL/g.

(Preparation of Polyamic Acid Solution D)
PMDA/m-ATDA

Polyamic acid solution D was prepared in a similar manner to the preparation of polyamic acid solution A except that pyromellitic dianhydride (PMDA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.72 dL/g.

(Preparation of Polyamic Acid Solution E)
6FDA/p-ATDA

Polyamic acid solution E was prepared in a similar manner to the preparation of polyamic acid solution A except that 4,4'-(hexafluoroisopropylidene)diphthalic dianhydride (6FDA) was used as an acid dianhydride. Logarithmic viscosity number ($\eta_{inh}$) of the polyamic acid was 0.54 dL/g.

(Preparation of Polyamic Acid Solution F)
6FDA/m-ATDA

Polyamic acid solution F was prepared in a similar manner to the preparation of polyamic acid solution A except that 4,4'-(hexafluoroisopropylidene)diphthalic dianhydride (6FDA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.57 dl/g.

(Preparation of Polyamic Acid Solution G)
CBDA/p-ATDA

Polyamic acid solution G was prepared in a similar manner to the preparation of polyamic acid solution A except that 1,2,3,4-cyclobutane tetracarboxylic dianhydride (CBDA) was used as an acid dianhydride. Logarithmic viscosity number ($\eta_{inh}$) of the polyamic acid was 1.54 dL/g.

(Preparation of Polyamic Acid Solution H)
CBDA/m-ATDA

Polyamic acid solution H was prepared in a similar manner to the preparation of polyamic acid solution A except that 1,2,3,4-cyclobutane tetracarboxylic dianhydride (CBDA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.65 dL/g.

(Preparation of Polyamic Acid Solution I)
s-BPDA/ODA

Polyamic acid solution I was prepared in a similar manner to the preparation of polyamic acid solution A except that 4,4'-diaminodiphenyl ether (ODA) was used as a diamine. Logarithmic viscosity number ($\eta_{inh}$) of the polyamic acid was 1.84 dL/g.

(Preparation of Polyamic Acid Solution N)
DSDA/m-ATDA

Polyamic acid solution N was prepared in a similar manner to the preparation of polyamic acid solution A except that 3,3',4,4'-diphenylsulfone-tetracarboxylic dianhydride (DSDA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.62 dL/g.

(Preparation of Polyamic Acid Solution O)
ODPA/m-ATDA

Polyamic acid solution O was prepared in a similar manner to the preparation of polyamic acid solution A except that 4,4'-oxydiphthalic dianhydride (ODPA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.66 dL/g.

(Preparation of Polyamic Acid Solution P)
BTDA/m-ATDA

Polyamic acid solution P was prepared in a similar manner to the preparation of polyamic acid solution A except that 3,3',4,4'-benzophenonetetracarboxylic dianhydride (BTDA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.60 dL/g.

(Preparation of Polyamic Acid Solution Q)
CHDA/m-ATDA

Polyamic acid solution Q was prepared in a similar manner to the preparation of polyamic acid solution A except that 1,2,4,5-cyclohexanetetracarboxylic dianhydride (CHDA) was used as an acid dianhydride and 2,4-bis(3-aminoanilino)-6-anilino-1,3,5-triazine (m-ATDA) was used as a diamine. Logarithmic viscosity number ($\eta_{inh}$) of the polyamic acid was 0.46 dL/g.

(Preparation of Polyamic Acid Solution R)
DSDA/p-ATDA

Polyamic acid solution R was prepared in a similar manner to the preparation of polyamic acid solution A except that 3,3',4,4'-diphenylsulfone-tetracarboxylic dianhydride (DSDA) was used as an acid dianhydride. Logarithmic viscosity number ($\eta_{inh}$) of the polyamic acid was 0.78 dL/g.

(Preparation of Polyamic Acid Solution S)
ODPA/p-ATDA

Polyamic acid solution S was prepared in a similar manner to the preparation of polyamic acid solution A except that 4,4'-oxydiphthalic dianhydride (ODPA) was used as an acid dianhydride. Logarithmic viscosity number ($\eta_{inh}$) of the polyamic acid was 0.84 dL/g.

(Preparation of Polyamic Acid Solution T)

BTDA/p-ATDA

Polyamic acid solution T was prepared in a similar manner to the preparation of polyamic acid solution A except that 3,3',4,4'-benzophenonetetracarboxylic dianhydride (BTDA) was used as an acid dianhydride. Logarithmic viscosity number ($\eta_{inh}$) of the polyamic acid was 0.64 dL/g.

(Preparation of Polyamic Acid Solution U)

CHDA/p-ATDA

Polyamic acid solution U was prepared in a similar manner to the preparation of polyamic acid solution A except that 1,2,4,5-cyclohexanetetracarboxylic dianhydride (CHDA) was used as an acid dianhydride. Logarithmic viscosity number ($\eta_{inh}$) of the polyamic acid was 0.50 dL/g.

The following polyimide and polyimide solution were prepared.

(Preparation of Polyimide V and Polyimide Solution V)

6FDA/m-ATDA

Into a three neck flask (100 mL) equipped with a three-one motor and a nitrogen inlet, 2,4-bis(3-aminoanilino)-6-anilino-1,3,5-triazine (m-ATDA) (0.961 g, 2.50 mmol) and N-methylpyrrolidone (NMP) (5 mL) were added under nitrogen stream and dissolved by stirring at room temperature. Then, to the mixture, 4,4'-(hexafluoroisopropylidene)diphthalic dianhydride (6FDA) (1.111 g, 2.50 mmol) was added with stirring at room temperature and further stirred at room temperature for 6 hours. Since the viscosity increases with the progress of the polymerization, the solvent was added and polyamic acid solution as polyimide precursor was obtained. Then, Dean-Stark apparatus and Dimroth condenser were equipped, and NMP was charged to the polyamic acid solution so that the reaction solution became 5 wt %. 5 mL of Toluene was added as azeotropic solvent and water was removed from the system by stirring at 140° C. for 3 hours, and further stirred at 200° C. for 3 hours to carry out imidization reaction. The reaction solution was poured into methanol to precipitate and solid matter was obtained after suction filtration. The obtained solid was dried in vacuo at room temperature to give polyimide V. Logarithmic viscosity number ($\eta_{inh}$) of polyimide V was 0.64 dL/g. Further, polyimide V was dissolved in NMP again to obtain polyimide solution V.

(Preparation of Polyimide W and Polyimide Solution W)

DSDA/m-ATDA

Polyimide W and polyimide solution W were prepared in a similar manner to the preparation of polyimide V and polyimide solution V except that 3,3',4,4'-diphenylsulfonetetracarboxylic dianhydride (DSDA) was used as an acid dianhydride. Logarithmic viscosity number ($\eta_{inh}$) of the polyimide W was 0.62 dL/g.

(Preparation of Polyimide X and Polyimide Solution X)

ODPA/m-ATDA

Polyimide X and polyimide solution X were prepared in a similar manner to the preparation of polyimide V and polyimide solution V except that 4,4'-oxydiphthalic dianhydride (ODPA) was used as an acid dianhydride. Logarithmic viscosity number ($\eta_{inh}$) of the polyimide X was 0.52 dL/g.

Preparation of Polyimide Film, and Evaluation of Solubility in Organic Solvent and Optical Property Comparative Example 1

Preparation of Polyimide Film A s-BPDA/p-ATDA

Polyamic acid solution A was cast as a thin film on a glass plate, and heated at 60° C. for 6 hours, 100° C. for 1 hour, 200° C. for 1 hour, and further 300° C. for 1 hour to perform thermal imidization. After cooling it, it was immersed in water to peel the polyimide film from the glass plate. The film was dried, giving polyimide film A having thickness of 16 μm.

The solubility to organic solvent and optical property of the obtained polyimide film were shown in Tables 1 and 2, respectively.

Example 1

Preparation of Polyimide Film B s-BPDA/m-ATDA

Polyimide film B having thickness of 14 μm was obtained after dried in similar manner as described for the preparation of polyimide film A except that polyamic acid solution B was used in place of polyamic acid solution A. The refractive index ($n_D$) of polyimide film B was 1.739. The solubility to organic solvent and optical property of the obtained polyimide film were shown in Tables 1 and 2, respectively.

Comparative Example 2

Preparation of Polyimide Film C

PMDA/p-ATDA

Polyimide film C having thickness of 14 μm was obtained after dried in similar manner as described for the preparation of polyimide film A except that polyamic acid solution C was used in place of polyamic acid solution A. The respective properties were shown in Tables 1 and 2.

Example 2

Preparation of Polyimide Film D

PMDA/m-ATDA

Polyimide film D having thickness of 17 μm was obtained after dried in similar manner as described for the preparation of polyimide film A except that polyamic acid solution D was used in place of polyamic acid solution A. The refractive index ($n_D$) of polyimide film D was 1.759. The respective properties were shown in Tables 1 and 2.

Comparative Example 3

Preparation of Polyimide Film E

6FDA/p-ATDA

Polyimide film E having thickness of 17 μm was obtained after dried in similar manner as described for the preparation of polyimide film A except that polyamic acid solution E was used in place of polyamic acid solution A. The respective properties were shown in Tables 1 and 2.

Example 3

Preparation of Polyimide Film F

6FDA/m-ATDA

Polyimide film F having thickness of 16 μm was obtained after dried in similar manner as described for the preparation of polyimide film A except that polyamic acid solution F was used in place of polyamic acid solution A. The refractive index ($n_D$) of polyimide film F was 1.728. The respective properties were shown in Tables 1 and 2.

Comparative Example 4

Preparation of Polyimide Film I s-BPDA/ODA

Polyimide film I having thickness of 37 μm was obtained after dried in similar manner as described for the preparation of polyimide film A except that polyamic acid solution I was used in place of polyamic acid solution A. The refractive index ($n_D$) of polyimide film I was 1.714. The respective properties were shown in Tables 1 and 2.

Preparation of Polyimide Film Using CBDA and ATDA

Referential Example 1

Preparation of Polyimide Film G

CBDA/p-ATDA

Polyimide film G having thickness of 10 μm was obtained after dried in similar manner as described for the preparation of polyimide film A except that polyamic acid solution G was used in place of polyamic acid solution A. The respective properties were shown in Tables 1 and 2.

Example 4

Preparation of Polyimide Film H

CBDA/m-ATDA

Polyimide film H having thickness of 11 μm was obtained after dried in similar manner as described for the preparation of polyimide film A except that polyamic acid solution H was used in place of polyamic acid solution A. The refractive index ($n_D$) of polyimide film H was 1.729. The respective properties were shown in Tables 1 and 2.

Evaluation of Glass Transition Temperature

Example 5

Preparation of Polyimide Film J s-BPDA/m-ATDA

Polyimide film J was obtained in similar manner as described in Example 1 except that the thickness of the polyimide film was changed to 40 μm. The glass transition temperature (DSC) of polyimide film J was 261° C.

Example 6

Preparation of Polyimide Film K

PMDA/m-ATDA

Polyimide film K was obtained in similar manner as described in Example 2 except that the thickness of the polyimide film was changed to 40 μm. The glass transition temperature (DSC) of polyimide film K was 291° C.

Example 7

Preparation of Polyimide Film L

6FDA/m-ATDA

Polyimide film L was obtained in similar manner as described in Example 3 except that the thickness of the polyimide film was changed to 40 μm. The glass transition temperature (DSC) of polyimide film L was 256° C.

Example 8

Preparation of Polyimide Film M

CBDA/m-ATDA

Polyimide film M was obtained in similar manner as described in Example 4 except that the thickness of the polyimide film was changed to 23 μm. The glass transition temperature (DSC) of polyimide film M was 288° C. The coefficient of linear thermal expansion of the film after annealing at 300° C. was measured. It showed low value of 14.1 ppm/K for the coefficient of linear thermal expansion of 50 to 200° C.

Manufacturing of Polyimide-Metal Laminate and Peeling Strength

Example 9 s-BPDA/m-ATDA

Polyimide-metal laminate was manufactured using polyamic acid solution B. Polyimide-metal laminate was obtained by coating a rolled copper foil (BHY-13H-T, 18 μm thickness; Manufactured by JX Nippon Mining & Metals Corporation) with polyamic acid solution B and heating at 120° C. for 10 min, and further raising a temperature up to 400° C. taking 20 min. The thickness of the polyimide film in the polyimide-metal laminate was 24 μm. The result of 90°-peeling test of the polyimide-metal laminate showed that it had good adhesiveness and the film was broken at 0.45 kN/m. Therefore, the polyimide-metal laminate is presumed to have the peeling strength of 0.45 kN/m or higher.

Example 10 s-BPDA/m-ATDA

Polyimide-metal laminate was manufactured using polyamic acid solution B. Polyimide-metal laminate was obtained by coating a rolled copper foil (BHY-13H-T, 18 μm thickness; Manufactured by JX Nippon Mining & Metals Corporation) with polyamic acid solution B and heating at 120° C. for 10 min, and further raising a temperature up to 400° C. taking 20 min. The thickness of the polyimide film in the polyimide-metal laminate was 47 μm. The result of 90°-peeling test of the polyimide-metal laminate showed that it had good adhesiveness and the film was broken at 1.35 kN/m. Therefore, the polyimide-metal laminate is presumed to have the peeling strength of 1.35 kN/m or higher.

Comparative Example 5 s-BPDA/PPD

Polyimide-metal laminate was manufactured using polyamic acid solution obtained from 3,3',4,4'-biphenyltetracarboxylic dianhydride (s-BPDA) as an aromatic tetracarboxylic dianhydride and para-phenylene diamine (PPD) as a diamine. Polyimide-metal laminate was obtained by coating a rolled copper foil (BHY-13H-T, 18 μm thickness; Manufactured by JX Nippon Mining & Metals Corporation) with the polyamic acid solution and heating at 120° C. for 10 min, and further raising a temperature up to 400° C. taking 20 min. The thickness of the polyimide film in the polyimide-metal laminate was 22 μm. The result of 90°-peeling test of the polyimide-metal laminate showed that the peeling strength was 0.1 kN/m or lower.

Example 11

Preparation of Polyimide Film N

DSDA/m-ATDA

Polyimide film N having thickness of 21 μm was obtained after dried in similar manner as described for the preparation of polyimide film A except that polyamic acid solution N was used in place of polyamic acid solution A. The refractive index ($n_D$) of polyimide film N was 1.724. The respective properties were shown in Tables 3 and 4. The glass transition temperature (DSC) of polyimide film N was 249° C.

Example 12

Preparation of Polyimide Film O

ODPA/m-ATDA

Polyimide film O having thickness of 18 μm was obtained after dried in similar manner as described for the preparation of polyimide film A except that polyamic acid solution O was used in place of polyamic acid solution A. The refractive index ($n_D$) of polyimide film O was 1.732. The respective properties were shown in Tables 3 and 4. The glass transition temperature (DSC) of polyimide film O was 253° C.

Example 13

Preparation of Polyimide Film P

BTDA/m-ATDA

Polyimide film P having thickness of 17 μm was obtained after dried in similar manner as described for the preparation of polyimide film A except that polyamic acid solution P was used in place of polyamic acid solution A. The refractive index ($n_D$) of polyimide film P was 1.730. The respective properties were shown in Tables 3 and 4. The glass transition temperature (DSC) of polyimide film P was 248° C.

Example 14

Preparation of Polyimide Film Q

CHDA/m-ATDA

Polyimide film Q having thickness of 21 μm was obtained after dried in similar manner as described for the preparation of polyimide film A except that polyamic acid solution Q was used in place of polyamic acid solution A. The respective properties were shown in Tables 3 and 4. In the solubility test of polyimide film Q, polyimide film Q was dissolved in NMP at room temperature and dissolved in an amount of 15 mass % or more.

Comparative Example 6

Preparation of Polyimide Film R

DSDA/p-ATDA

Polyimide film R was obtained in similar manner as described for the preparation of polyimide film A except that polyamic acid solution R was used in place of polyamic acid solution A. The respective properties were shown in Tables 3 and 4. The glass transition temperature (DSC) of polyimide film R was 291° C.

Comparative Example 7

Preparation of Polyimide Film S

ODPA/p-ATDA

Polyimide film S having thickness of 16 μm was obtained after dried in similar manner as described for the preparation of polyimide film A except that polyamic acid solution S was used in place of polyamic acid solution A. The respective properties were shown in Table 3. The glass transition temperature (DSC) of polyimide film S was 257° C.

Comparative Example 8

Preparation of Polyimide Film T

BTDA/p-ATDA

Polyimide film T having thickness of 21 μm was obtained after dried in similar manner as described for the preparation of polyimide film A except that polyamic acid solution T was used in place of polyamic acid solution A. The respective properties were shown in Tables 3 and 4. The glass transition temperature (DSC) of polyimide film T was 268° C.

Referential Example 2

Preparation of Polyimide Film U

CHDA/p-ATDA

Polyimide film U was obtained in similar manner as described for the preparation of polyimide film A except that polyamic acid solution U was used in place of polyamic acid solution A. The respective properties were shown in Table 3.

Preparation of Polyimide Film from Polyimide Solution, and Evaluation of Solubility in Organic Solvent

Example 15

Preparation of Polyimide Film V

6FDA/m-ATDA

Polyimide solution V was cast as a thin film on a glass plate, and heated in a vacuum oven at 60° C. for 6 hours, 100° C. for 1 hour, 200° C. for 1 hour, and further 300° C. for 1 hour to obtain polyimide film V having thickness of 40 μm. The glass transition temperature (DSC) of polyimide film V was 250° C.

The solubility of polyimide V in organic solvent was shown in Table 5. In the solubility test of polyimide film V, polyimide film V was dissolved in NMP at room temperature and dissolved in an amount of 20 weight % or more.

Example 16

Preparation of Polyimide Film W

DSDA/m-ATDA

Polyimide film W was obtained in similar manner as described for the preparation of polyimide film V except that polyimide solution W was used in place of polyimide solution V. The glass transition temperature (DSC) of polyimide film W was 244° C.

The solubility of polyimide W in organic solvent was shown in Table 5.

Example 17

Preparation of Polyimide Film X

ODPA/m-ATDA

Polyimide film X was obtained in similar manner as described for the preparation of polyimide film V except that polyimide solution X was used in place of polyimide solution V. The glass transition temperature (DSC) of polyimide film X was 253° C.

The solubility of polyimide X in organic solvent was shown in Table 5.

Manufacturing of Polyimide-Metal Laminate and Evaluation of Peeling Strength

Example 18

PMDA/m-ATDA

Polyimide-metal laminate was manufactured using polyamic acid solution D. Polyimide-metal laminate was obtained by coating a rolled copper foil (BHY-13H-T, 18 μm thickness; Manufactured by JX Nippon Mining & Metals Corporation) with polyamic acid solution D and heating at 120° C. for 10 min, and further raising a temperature up to 400° C. taking 20 min. The thickness of the polyimide film in the polyimide-metal laminate was 40 μm. The result of 90°-peeling test of the polyimide-metal laminate showed that it had good adhesiveness and the film was broken at 0.68 kN/m. Therefore, the polyimide-metal laminate is presumed to have the peeling strength of 0.68 kN/m or higher.

Example 19

6FDA/m-ATDA

Polyimide-metal laminate was manufactured in similar manner as described in Example 18 except that polyamic acid solution F was used in place of polyamic acid solution D and peeling test was carried out. The result showed that it had good adhesiveness and the film was broken at 0.54 kN/m. Therefore, the polyimide-metal laminate is presumed to have the peeling strength of 0.54 kN/m or higher.

Example 20

DSDA/m-ATDA

Polyimide-metal laminate was manufactured in similar manner as described in Example 18 except that polyamic acid solution N was used in place of polyamic acid solution D and peeling test was carried out. The result showed that it had good adhesiveness and the film was broken at 0.42 kN/m. Therefore, the polyimide-metal laminate is presumed to have the peeling strength of 0.42 kN/m or higher.

Example 21

ODPA/m-ATDA

Polyimide-metal laminate was manufactured in similar manner as described in Example 18 except that polyamic acid solution O was used in place of polyamic acid solution D and peeling test was carried out. The result showed that it had good adhesiveness and the film was broken at 1.35 kN/m. Therefore, the polyimide-metal laminate is presumed to have the peeling strength of 1.35 kN/m or higher.

Example 22

BTDA/m-ATDA

Polyimide-metal laminate was manufactured in similar manner as described in Example 18 except that polyamic acid solution P was used in place of polyamic acid solution D and peeling test was carried out. The result showed that it had good adhesiveness and the film was broken at 1.29 kN/m. Therefore, the polyimide-metal laminate is presumed to have the peeling strength of 1.29 kN/m or higher.

Manufacturing of Two-Layered Polyimide Laminate and Evaluation of Peeling Strength

Example 23

PMDA/m-ATDA

Two-layered polyimide laminate was manufactured using polyamic acid solution D. Except that a polyimide film (Upilex75S, 75 μm thickness; manufacture by UBE Industries, Ltd.) was coated with polyamic acid solution D, a two-layered polyimide laminate was obtained in similar manner as described in Example 18, and the peeling test was conducted. The result showed that it had good adhesiveness and the film was broken at 0.62 kN/m. Therefore, the two-layered polyimide laminate is presumed to have the peeling strength of 0.62 kN/m or higher.

Example 24

6FDA/m-ATDA

Two-layered polyimide laminate was manufactured using polyamic acid solution F. Except that a polyimide film (Upilex75S, 75 μm thickness; manufacture by UBE Industries, Ltd.) was coated with polyamic acid solution F, a two-layered polyimide laminate was obtained in similar manner as described in Example 18, and the peeling test was conducted. The result showed that it had good adhesiveness and the film was broken at 0.55 kN/m. Therefore, the two-layered polyimide laminate is presumed to have the peeling strength of 0.55 kN/m or higher.

Example 25

DSDA/m-ATDA

Two-layered polyimide laminate was manufactured using polyamic acid solution N. Except that a polyimide film (Upilex75S, 75 μm thickness; manufacture by UBE Industries, Ltd.) was coated with polyamic acid solution N, a two-layered polyimide laminate was obtained in similar manner as described in Example 18, and the peeling test was conducted. The result showed that it had good adhesiveness and the film was broken at 0.37 kN/m. Therefore, the two-layered polyimide laminate is presumed to have the peeling strength of 0.37 kN/m or higher.

Example 26

ODPA/m-ATDA

Two-layered polyimide laminate was manufactured using polyamic acid solution O. Except that a polyimide film (Upilex75S, 75 μm thickness; manufacture by UBE Industries, Ltd.) was coated with polyamic acid solution O, a two-layered polyimide laminate was obtained in similar manner as described in Example 18, and the peeling test was conducted. The result showed that it had good adhesiveness and the film was broken at 0.28 kN/m. Therefore, the two-layered polyimide laminate is presumed to have the peeling strength of 0.28 kN/m or higher.

Comparative Example 9 s-BPDA/PPD

Two-layered polyimide laminate was manufactured using polyamic acid solution obtained from 3,3',4,4'-biphenyltetracarboxylic dianhydride (s-BPDA) as an aromatic tetracarboxylic dianhydride and para-phenylene diamine (PPD) as a diamine. Except that a polyimide film (Upilex75S, 75 μm thickness; manufacture by UBE Industries, Ltd.) was coated with this polyamic acid solution, a two-layered polyimide laminate was obtained in similar manner as described in Example 18, and the peeling test was conducted. The result showed that the peeling strength was 0.02 kN/m or lower.

TABLE 1

| Example | polyimide | diamine | acid anhydride | DMAc | NMP | THF | CHCl₃ |
|---|---|---|---|---|---|---|---|
| Comp. Ex 2 | C | p-ATDA | PMDA | ± | ± | − | − |
| Comp. Ex 1 | A | p-ATDA | s-BPDA | ++ | ++ | − | − |
| Comp. Ex 3 | E | p-ATDA | 6FDA | ++ | + | ± | − |
| Example 2 | D | m-ATDA | PMDA | ± | ± | − | − |
| Example 1 | B | m-ATDA | s-BPDA | + | + | − | − |
| Example 3 | F | m-ATDA | 6FDA | ++ | + | ++ | ± |
| Comp. Ex 5 | I | ODA | s-BPDA | ± | ± | − | − |
| Ref. Ex 1 | G | p-ATDA | CBDA | ++ | ++ | − | − |
| Example 4 | H | m-ATDA | CBDA | + | + | − | − |

Comp. Ex = Comparative Example, Ref. Ex = Referential Example

TABLE 2

| | | | polyimide film | | | | |
|---|---|---|---|---|---|---|---|
| | | | thickness (μm) | wavelength | | transmittance | | |
| | acid component | diamine component | | λcutoff (nm) | λ₈₀% (nm) | 400 nm (%) | 500 nm (%) | 600 nm (%) |
| Synthesis Ref. Ex 2 | — | p-ATDA | — | 328 | 346 | 93 | 98 | 100 |
| Synthesis Example 1 | — | m-ATDA | — | 312 | 366 | 99 | 100 | 100 |
| Comp. Ex 1 | s-BPDA | p-ATDA | 16 | 392 | 464 | 0 | 91 | 96 |
| Example 1 | s-BPDA | m-ATDA | 14 | 376 | 452 | 5 | 92 | 99 |
| Comp. Ex 2 | PMDA | p-ATDA | 14 | 496 | 596 | 0 | 0 | 83 |
| Example 2 | PMDA | m-ATDA | 17 | 396 | 524 | 0 | 53 | 99 |
| Comp. Ex 3 | 6FDA | p-ATDA | 17 | 440 | 516 | 0 | 65 | 94 |
| Example 3 | 6FDA | m-ATDA | 16 | 424 | 520 | 11 | 94 | 99 |
| Ref. Ex 1 | CBDA | p-ATDA | 10 | 328 | 384 | 85 | 95 | 97 |
| Example 4 | CBDA | m-ATDA | 11 | 300 | 360 | 88 | 95 | 98 |

TABLE 3

| Example | polyimide | diamine | acid anhydride | DMAc | NMP | THF | CHCl₃ |
|---|---|---|---|---|---|---|---|
| Example 11 | N | m-ATDA | DSDA | + | + | − | − |
| Example 12 | O | m-ATDA | ODPA | + | + | − | − |
| Example 13 | P | m-ATDA | BTDA | ± | ± | − | − |
| Example 14 | Q | m-ATDA | CHDA | ++ | ++ | − | − |
| Comp. Ex 6 | R | p-ATDA | DSDA | + | + | − | − |
| Comp. Ex 7 | S | p-ATDA | ODPA | + | + | − | − |
| Comp. Ex 8 | T | p-ATDA | BTDA | ± | ± | − | − |
| Ref. Ex 2 | U | p-ATDA | CHDA | + | + | − | − |

TABLE 4

| | | polyimide film | | | | | |
|---|---|---|---|---|---|---|---|
| | | thick- | wavelength | | transmittance | | |
| | acid component | diamine component | ness (μm) | λcutoff (nm) | λ$_{80\%}$ (nm) | 400 nm (%) | 500 nm (%) | 600 nm (%) |
| Example 11 | DSDA | m-ATDA | 21 | 432 | 660 | 0 | 41 | 75 |
| Example 12 | ODPA | m-ATDA | 18 | 358 | 780 | 10 | 61 | 71 |
| Example 13 | BTDA | m-ATDA | 17 | 428 | 732 | 0 | 36 | 65 |
| Example 14 | CHDA | m-ATDA | 21 | 316 | 504 | 71 | 78 | 81 |
| Comp. Ex 6 | DSDA | p-ATDA | 19 | 480 | 680 | 0 | 25 | 70 |
| Comp. Ex 8 | BTDA | p-ATDA | 21 | 500 | 750 | 0 | 30 | 62 |

TABLE 5

| Example | polyimide | diamine | acid anhydride | DMAc | NMP | THF | CHCl₃ |
|---|---|---|---|---|---|---|---|
| Example 15 | V | m-ATDA | 6FDA | ++ | ++ | ++ | ± |
| Example 16 | W | m-ATDA | DSDA | + | + | − | − |
| Example 17 | X | m-ATDA | ODPA | + | + | − | − |

Figure 2:
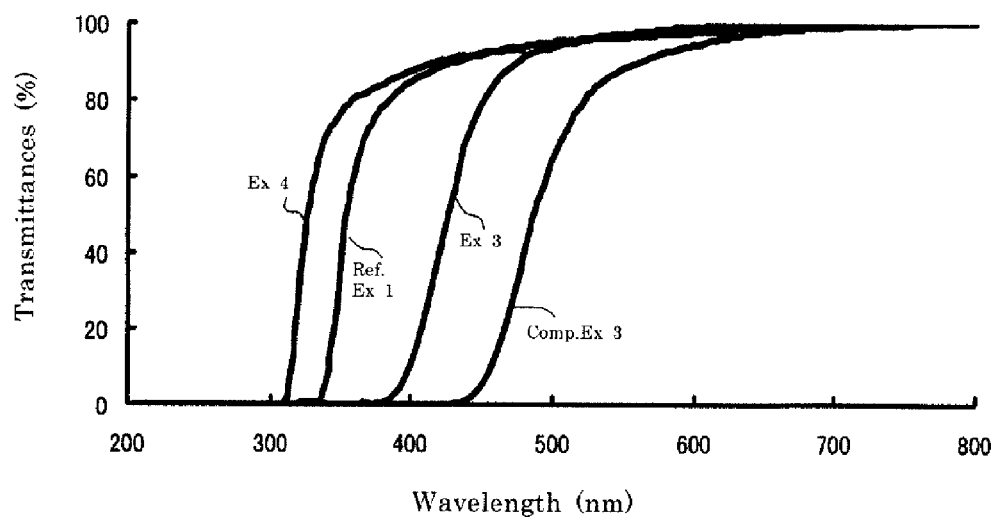
FIG. 2 shows UV-visible spectra of the polyimide films of the present invention.
Figure 3:
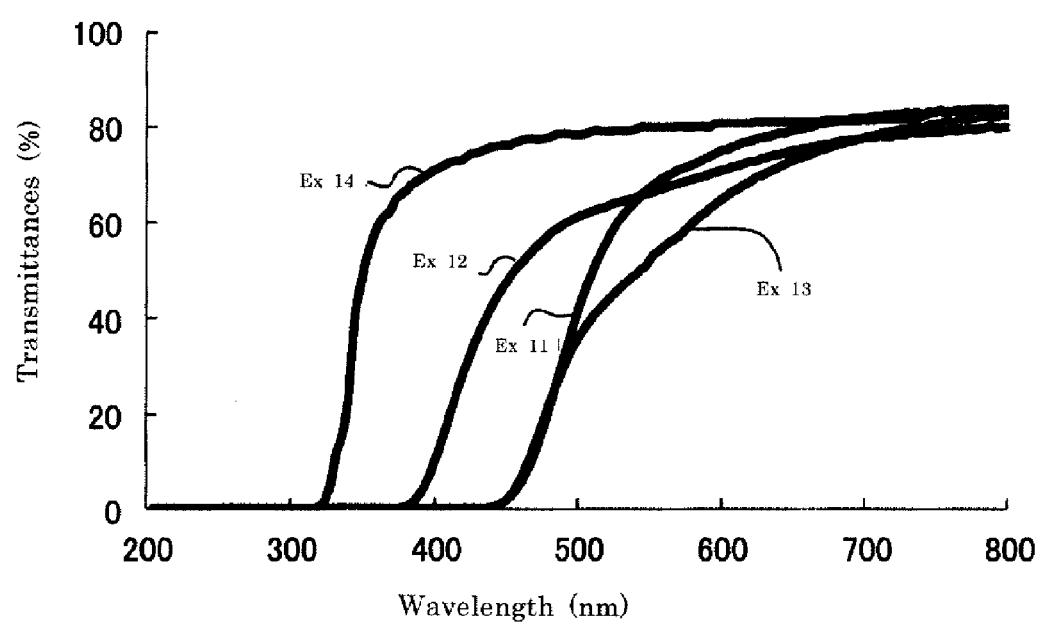
FIG. 3 shows UV-visible spectra of the polyimide films of the present invention.

FIGS. 1, 2, and 3 show the transmittances of the polyimide films that are shown in Tables 2 and 4. As evident from Tables 2 and 4 and FIGS. 1, 2, and 3, the polyimide films obtained using m-ATDA of the present invention have higher transmittance than those obtained using p-ATDA.

As evident from the results of the peeling strength of the polyimide-metal laminates, the polyimide films of the present invention have high peeling strength.

The invention claimed is:

1. A polyimide precursor comprising a structural unit represented by general formula (I):

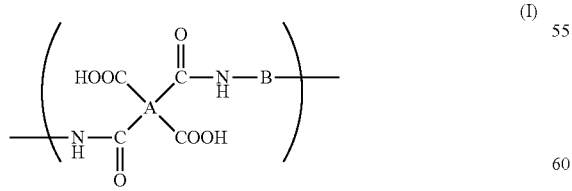

in which A is a tetravalent aromatic group and B is a divalent aromatic group, wherein B in general formula (I) comprises a triazine moiety represented by following formula (B1):

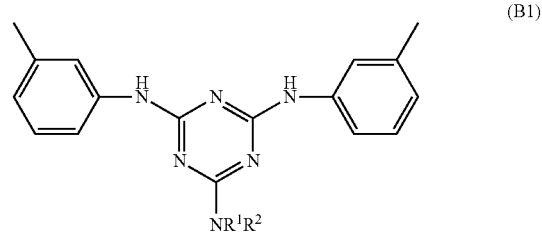

in which $R^1$ denotes hydrogen or alkyl or aryl having 1 to 12 carbon atoms, and $R^2$ denotes hydrogen or alkyl or aryl having 1 to 12 carbon atoms, and A in general formula (I) comprises a tetravalent residue obtainable by removing two carboxylic anhydride groups from 2,2-bis(3,4-dicarboxyphenyl)-1,1,1,3,3,3-hexafluoropropane dianhydride.

2. A polyimide precursor comprising a structural unit represented by general formula (I):

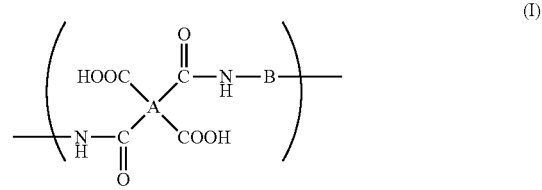

in which A is a tetravalent aliphatic group and B is a divalent aromatic group, wherein B in general formula (I) comprises a triazine moiety represented by following formula (B1):

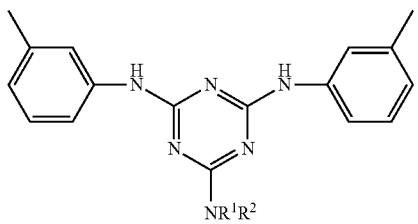

(B1)

in which $R^1$ denotes hydrogen or alkyl or aryl having 1 to 12 carbon atoms, and $R^2$ denotes hydrogen or alkyl or aryl having 1 to 12 carbon atoms.

3. A polyimide precursor according to claim 2, wherein A in general formula (I) comprises a tetravalent residue obtainable by removing two carboxylic anhydride groups from at least one of cyclohexanetetracarboxylic dianhydride and 1,2,3,4-cyclobutanetetracarboxylic dianhydride.

4. A polyimide precursor according to claim 1, wherein $R^1$ denotes hydrogen and $R^2$ denotes phenyl in general formula (B1).

5. A polyimide precursor according to claim 1, wherein B in general formula (I) comprises the triazine moiety represented by general formula (B1) in an amount of 10 to 100 mol %.

6. A polyimide obtainable from the polyimide precursor according to claim 1, comprising a structural unit represented by general formula (II):

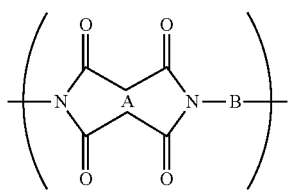

(II)

in which A and B are groups as defined in claim 1.

7. A polyimide film comprising the polyimide according to claim 6.

8. A metal laminate comprising the polyimide film according to claim 7 and metal layer laminated on the polyimide film directly or via an adhesive.

9. A method for producing 2,4-bis(3-aminoanilino)-6-substituted amino-1,3,5-triazine represented by general formula (B2), comprising:

reacting 6-substituted amino-1,3,5-triazine-2,4-dihalide represented by general formula (B3) with 3-nitroaniline to form 2,4-bis-(3-nitroanilino)-6-substituted amino-1,3,5-triazine represented by general formula (B4); and reducing the obtained 2,4-bis-(3-nitroanilino)-6-substituted amino-1,3,5-triazine;

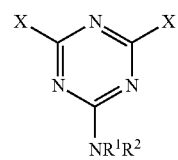

(B3)

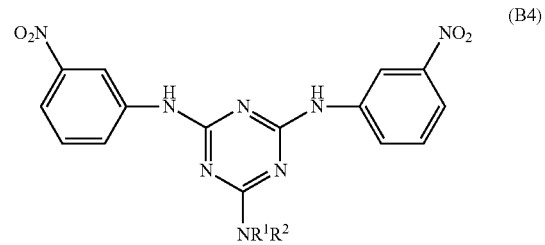

(B4)

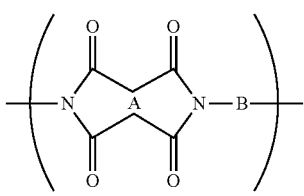

(B2)

in which $R^1$ denotes hydrogen or alkyl or aryl having 1 to 12 carbon atoms, $R^2$ denotes hydrogen or alkyl or aryl having 1 to 12 carbon atoms, and X denotes halogen atom.

10. A polyimide precursor according to claim 2, wherein $R^1$ denotes hydrogen and $R^2$ denotes phenyl in general formula (B1).

11. A polyimide precursor according to claim 2, wherein B in general formula (I) comprises the triazine moiety represented by general formula (B1) in an amount of 10 to 100 mol %.

12. A polyimide obtainable from the polyimide precursor according to claim 2, comprising a structural unit represented by general formula (II):

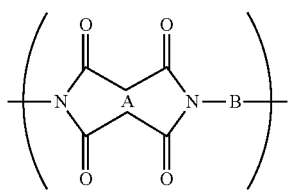

(II)

in which A and B are groups as defined in claim 2.

13. A polyimide film comprising the polyimide according to claim 12.

14. A metal laminate comprising the polyimide film according to claim 13 and metal layer laminated on the polyimide film directly or via an adhesive.

\* \* \* \* \*